(12) United States Patent
Del Soldato

(10) Patent No.: US 7,399,878 B2
(45) Date of Patent: *Jul. 15, 2008

(54) PHARMACEUTICAL COMPOUNDS

(75) Inventor: Piero Del Soldato, Milan (IT)

(73) Assignee: Nicox S.A., Sophia Antipolis - Valbonne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/642,783

(22) Filed: Dec. 21, 2006

(65) Prior Publication Data

US 2007/0197499 A1 Aug. 23, 2007

Related U.S. Application Data

(63) Continuation of application No. 10/048,469, filed as application No. PCT/EP00/07225 on Jul. 27, 2000, now Pat. No. 7,186,753.

(30) Foreign Application Priority Data

Aug. 12, 1999 (IT) .............................. MI99A1817

(51) Int. Cl.
C07C 203/00 (2006.01)
(52) U.S. Cl. ...................................... 558/482; 558/483
(58) Field of Classification Search ........................ None
See application file for complete search history.

(56) References Cited

U.S. PATENT DOCUMENTS

| | | | |
|---|---|---|---|
| 5,597,847 | A | 1/1997 | Matji |
| 5,700,947 | A | 12/1997 | Del Soldato |
| 5,861,426 | A | 1/1999 | Del Soldato et al. |
| 6,242,432 | B1 | 6/2001 | Del Soldato |
| 7,186,753 | B1 * | 3/2007 | Del Soldato ................ 514/509 |

FOREIGN PATENT DOCUMENTS

| | | |
|---|---|---|
| EP | 0 012 866 A1 | 7/1980 |
| HU | 218 923 B | 9/1994 |
| WO | WO 98/15568 A2 | 4/1998 |

OTHER PUBLICATIONS

Baylis, Christine et al., "Chronic Blockade of Nitric Oxide Synthesis in the Rat Produces Systemic Hypertension and Glomerular Damage," The American Society for Clinical Investigation, Inc., vol. 90, Jul. 1992, pp. 278-281.
Benoni, Giuseppina et al., "Plasma Concentrations and Pharmacokinetic Parameters of Nitrofenac Using a Simple and Sensitive HPLC Method," Journal of Pharmaceutical Sciences, vol. 84, No. 1, Jan. 1995, pp. 93-95.
Cirino, G. et al., "Inhibition of inducible nitric oxide synthase expression by novel nonsteroidal anti-inflammatory derivatives with gastrointestinal-sparing properties," British Journal of Pharmacology, vol. 117, No. 7, Apr. 1996, pp. 1421-1426.
Current Medical Diagnosis & Treatment 1998, 37th Edition, pp. 431 and 794.
Maffei, Facino R. et al., "Hydroxynimesulide, the Main Metabolite of Nimesulide, Prevents Hydroperoxide/Hemoglobin-Induced Hemolysis of Rat Erthrocytes," Drugs Exptl. Clin. Res. XXIII (5/8), 1997, pp. 157-165.
Goodman's & Gilman's The Pharmacological Basis of Therapeutics, Ninth Edition, 1996, p. 1474.
Greene, Theodora W. et al., Protective Groups in Organic Synthesis, Second Edition, 1980.
Halliwell, Barry et al., Free Radicals in Biology and Medicine, Second Edition, 1989, pp. 86-87, and 416-417.
Hermann, Corinna et al., "Shear Stress Inhibits $H_2O_2$-Induced Apoptosis of Human Endothelial Cells by Modulation of the Glutathione Redox Cycle and Nitric Oxide Synthase," Arteriosclerosis, Thrombosis and Vasular Biology, vol. 17, No. 12, Dec. 1997, pp. 3588-3592.
McCance, Kathryn L. et al., Pathophysiology The Biologic Basis for Disease in Adults and Children, Third Edition, 1988, pp. 48-54.
McCance, Kathryn L. et al., Pathophysiology The Biologic Basis for Disease in Adults and Children, Third Edition, 1988, pp. 71-77.
McCance, Kathryn L. et al., Pathophysiology The Biologic Basis for Disease in Adults and Children, Third Edition, 1988, p. 1025.
Martindale The Extra Pharmacopoeia, Thirtieth Edition, Royal Pharmaceutical Society, "Corticosteroids," 1993, pp. 712-723.
Martindale The Extra Pharmacopoeia, Thirty-first Edition, Royal Pharmaceutical Society, "Nonsteroidal Anti-inflammatory Drugs," 1996, p. 73.
Schimmer, Bernard P. et al., "Adrenocorticotropic Hormone; Adrenocortical Steroids and Their Synthetic Analogs; Inhibitors of the Synthesis and Actions of Adrenocortical Hormones," Goodman & Gilman's The Pharmacological Basis of Therapeutics, Ninth Edition, 1996, pp. 1459-1465.
Schwarz, Kathleen B., "Oxidative Stress During Viral Infection: A Review," Free Radical Biology & Medicine, vol. 21, No. 5, 1996, pp. 641-649.
Silverstein, Fred E. et al., "Misoprostol Reduces Serious Gastrointestinal Complications in Patients with Rheumatoid Arthritis Receiving Nonsteroidal Anti-Inflammatory Drugs," Annals of Internal Medicine, vol. 123, No. 4, Aug. 15, 1995, pp. 241-249.
Utley, Henry G. et al., "Effect of Sulfhydryl Reagents on Peroxidation in Microsomes," Archives of Biochemistry and Biophysics, 118, 1967, pp. 29-32.

* cited by examiner

Primary Examiner—Paul A Zucker
(74) Attorney, Agent, or Firm—Arent Fox LLP

(57) ABSTRACT

Compounds or their salts of general formula (I): $A-B-N(O)_s$ wherein: s is an integer equal to 1 or 2; $A=R-T_1-$, wherein R is the drug radical and $T_1=(CO)_t$ or $(X)_t$, wherein X=O, S, $NR_{1c}$, $R_{1c}$ is H or a linear or branched alkyl or a free valence, t and t' are integers and equal to zero or 1, with the proviso that t=1 when t'=0; t=0 when t'=1; $B=-T_B-X_2-$O— wherein $T_B=$ (CO) when t=0, $T_B=X$ when t'=0, X being as above defined; $X_2$ is equal to $R_{1B-X-R2B}$ radical wherein X is as above defined, $R_{1B}$ and $R_{2B}$, equal to or different from each other, are linear or branched $C_1$-$C_6$ alkylenes, or $X_2$ is a radical wherein two alkylene chains $C_1$-$C_4$ are linked to nonadjacent positions of a central ring having 4 or 6 atoms, said ring being an unsaturated cycloaliphatic ring, or a saturated or aromatic heterocylic ring, containing one or two heteroatoms, equal or different, selected from O, S, N; wherein the unsaturated cycloaliphatic ring does not have aromatic character according to Huckel's rule.

7 Claims, No Drawings

PHARMACEUTICAL COMPOUNDS

This is a Continuation of application Ser. No. 10/048,469 filed Feb. 7, 2002 now U.S. Pat. No. 7,186,753, which is a National Stage of Application No. PCT/EP00/07225 filed Jul. 27, 2000. The disclosures of the prior applications are hereby incorporated by reference herein in their entirety.

The present invention relates to novel drugs for systemic use and non systemic use, and the composition thereof, to be used in oxidative stress and/or endothelial dysfuntions of moderate intensity.

By oxidative stress it is meant the generation of free radicals or radicalic compounds, which causes injury both of the cell and that of the surrounding tissue (Pathophysiology: the biological basis for disease in adults and children, McCance & Huether 1998 pages 48-54).

By endothelial dysfunctions it is meant those relating to the vasal endothelium. The damage of the vasal endothelium is known as one of those important events that can cause a series of pathological processes affecting various organs and body apparatuses, as described hereinafter (Pathophysiology: The biological basis for disease in adults and children, McCance & Huether 1998 page 1025).

As known, the oxidative stress and/or the endothelial dysfunctions are associated to various pathologies as reported hereinafter. The oxidative stress can also be caused by toxicity of a great variety of drugs, which significantly affects their performances.

Said pathological events are of a chronic, debilitating character and are very often typical of the elderly. As already said, in said pathological conditions the drugs used show a remarkably worsened performance.

Examples of pathological situations caused by the oxidative stress and/or by the endothelial dysfunctions, or present in elderly, are the following:

For the cardiovascular system: myocardial and vascular ischaemia in general, hypertension, stroke, arteriosclerosis, etc.

For the connective tissue: rheumatoid arthritis and connected inflammatory diseases, etc.

For the pulmonary system: asthma and connected inflammatory diseases, etc.

For the gastrointestinal system: ulcerative and non ulcerative dyspepsias, intestinal inflammatory diseases, etc.

For the central nervous system: Alzheimer disease, etc.

For the urogenital system: impotence, incontinence.

For the cutaneous system: eczema, neurodermatitis, acne.

The infective diseases in general (ref.: Schwarz-KB, Brady "Oxidative stress during viral infection: A review" Free radical Biol. Med. 21/5, 641-649 1996).

Further, the ageing process can be considered as a true pathologic condition (ref. Pathophysiology: the biological basis for disease in adults and children, pages 71-77).

The known drugs when administered to patients having pathologies associated to oxidative stress and/or endothelial dysfunctions, show a lower activity and/or higher toxicity.

This happens for example for drugs such as the antiinflammatory, cardiovascular drugs, respiratory apparatus drugs, central nervous system drugs, bone system drugs, antibiotics, urogenital, endocrine drugs, etc.

Drug research is directed to find new molecules having an improved therapeutic index (efficacy/toxicity ratio) or a lower risk/benefit ratio, also for pathological conditions as those above mentioned, wherein the therapeutic index of a great number of drugs results lowered. In fact in the above mentioned conditions of oxidative stress and/or endothelial dysfunctions, many drugs show a lower activity and/or higher toxicity.

For instance antiinflammatory drugs, such as NSAIDs and anticolitic drugs, such as 5-aminosalicylic acid and its derivatives, show the following drawbacks. NSAIDs result toxic particularly when the organism is debilitated or affected by morbid conditions associated to oxidative stress. Said conditions are for example the following: age, pre-existing ulcer, pre-existing gastric bleeding, debilitating chronic diseases such as in particular those affecting cardiovascular, renal apparatuses, the haematic crasis, etc. ("Misoprostol reduces serious gastrointestinal complications in patients with rheumatoid arthritis receiving non-steroidal anti-inflammatory drugs. A randomized, double blind, placebo-controlled trial." F. E. Silverstein et Al., Ann. Intern. Med. 123/4, 241-9, 1995; Martindale 31a ed. 1996, pag. 73, Current Medical Diagnosis and Treatment 1998, pages 431 and 794).

The administration of anti-inflammatory drugs to patients in the above mentioned pathological conditions can be made only at doses lower than those used in therapy in order to avoid remarkable toxicity phenomena. Thus anti-inflammatory activity results poor.

Beta-blockers, used for the angina, hypertension and cardiac arrhythmia treatment, show side effects towards the respiratory apparatus (dyspnoea, bronchoconstriction), and therefore they can give problems in patients affected by pathologies to said organs (asthma, bronchitis). Therefore beta-blockers further worsen respiratory diseases such as asthma. Therefore in asthmatic patients reduced doses of said drugs must be used in order not to jeopardize even more the respiratory functionality. Thus the efficacy of the beta-blockers results very reduced.

Antithrombotics, such as for example dipyridamole, aspirin, etc., used for the prophylaxis of thrombotic phenomena, have the same drawbacks. In patients affected by pathologies connected to oxidative stress and/or endothelial dysfunctions, the therapeutic action or the tolerability of these drugs, as in the case of aspirin, is greatly reduced.

Bronchodilators for example salbutamol, etc., are used in the asthma and bronchitis treatment and drugs active on the cholinergic system are used in pathologies such as urinary cholinergic incontinence. Their administration can produce similar side effects affecting the cardiovascular apparatus, causing problems both to cardiopathic and to hypertensive patients. Cardiopathies and hypertension are pathologies associated, as above said, to the oxidative stress and/or endothelial dysfunctions. Also these drugs show the same drawbacks as those above mentioned.

Expectorant and mucolytic drugs, which are used in the therapy. of inflammatory states of the respiratory organs, show drawbacks in patients affected by the above described conditions. Their administration can give rise to heartburn and gastric irritability, particularly in the elderly.

Bone resorption inhibitors, such as diphosphonates (for example alendronate, etc.) are drugs showing high gastrointestinal toxicity. Therefore also these drugs can show the same drawbacks as those above mentioned.

Phosphodiesterase inhibitors, such as for example sildenafil, zaprinast, used in the cardiovascular and respiratory system diseases, are charaterized by similar problems as to tolerability and/or efficacy in the mentioned pathological conditions of oxidative stress and/or endothelial disfunctions.

Antiallergic drugs, for example cetirizine, montelukast, etc. show similar problems in the mentioned pathological conditions, particularly for that it concerns their efficacy.

Anti-angiotensin drugs, f.i. ACE-inhibitors, for example enalapril, captopril, etc., and receptor inhibitors, for example losartan, etc., are used in the cardiovascular disease treatment. Their drawback is to give side effects to the respiratory apparatus (i.e. cough, etc.) in the above mentioned pathological conditions.

Antidiabetic drugs, both of the insulin-sensitizing and of hypoglycaemizing type, such as for example sulphonylureas, tolbutamide, glypiride, glyclazide, glyburide, nicotinamide etc., are ineffective in the prophylaxis of diabetic complications. Their administration can give side effects, such as for example gastric lesions. These phenomena become more intense in the pathological conditions above mentioned.

Antibiotics, for example ampicillin, clarihtromycin, etc., and antiviral drugs, acyclovir, etc., show problems as regards their tolerability, for example they cause gastrointestinal irritability.

Antitumoral drugs, for example doxorubicine, daunorubicin, cisplatinum, etc., have high toxicity, towards different organs, among which are stomach and intestine. Said toxicity is further worsened in the above mentioned pathologies of oxidative stress and/or endothelial dysfunctions.

Antidementia drugs for example nicotine and colinomimetics, are characterized by a poor tolerability especially in the above mentioned pathologies.

Drugs having a steroidal structure which are used in the therapy of acute diseases (asthma, etc.) or chronic diseases (intestinal, hepatic, respiratory diseases, female reproductive apparatus diseases, hormonal dysfunctions, cutaneous diseases, etc.) are characterized by remarkable toxic effects affecting various organs, particularly in the above mentioned oxidative stress conditions.

This class of steroidal drugs, among which hydrocortisone, cortisone, prednisone, prednisolone, fludrocortisone, desoxicorticosterone, methylprednisolone, triamcinolone, paramethasone, betamethasone, dexamethasone, triamcinolone acetonide, fluocinolone acetonide, beclomethasone, acetoxypregnelone, etc., has remarkable farmaco-toxicological effects on various organs and for this reason the clinical use and its interruption cause a series of side effects, some of which very serious. See for example Goodman & Gilman, "The pharmaceutical Basis of Therapeutics" 9° ed., pag. 1459-1465, 1996.

Among these toxic effects it can be mentioned: those affecting the bone tissue leading to an altered cellular metabolism and high osteoporosis incidence; those affecting the cardiovascular system generating hypertensive responses; those affecting the gastrointestinal apparatus giving gastric damages.

See for example Martindale "The extrapharmacopoeia", 30th ed., pag. 712-723, 1993.

Also biliary acids, which are used in hepatic trouble therapy and in biliary colics, belong to steroidal drugs. The ursodesoxycholic acid is also used in some hepatic troubles (hepatic cirrhosis of biliary origin, etc.). Their tolerability is strongly worsened in the presence of gastrointestinal complications (chronic hepatic damage, peptic ulcer, intestinal inflammation, etc.). Also in the case of biliary acids the oxidative stress notably affects the product performance: both the efficacy and the tolerability of the chenodeoxycholic and ursodesoxycholic acids are meaningfully reduced. In particular the undesired effects affecting liver result exalted. Among steroidal structures also estrogens used for the dislipidaemia, hormonal troubles, female apparatus tumours treatment can be mentioned. Also these steroids show side effects as above mentioned, in particular at hepatic level.

According to the above mentioned prior art, it seems almost impossible to separate therapeutic actions from side effects, see Goodman et al, above mentioned, at p. 1474.

The need was felt to have available drugs showing an improved therapeutic performance, i.e. endowed both of a lower toxicity and/or higher efficacy, so that they could be administered to patients in morbid conditions of oxidative stress and/or endothelial dysfunctions of moderate intensity, without showing the drawbacks of the drugs of the prior art.

It has now surprisingly and unexpectedly found that the aforementioned problems evidenced following the administration of drugs, to patients affected by oxidative stress and/or endothelial dysfucntions, or to the elderly in general, are solved by a novel class of drugs as described hereinafter.

An object of the invention are compounds or their salts having the following general formula (I):

$$A\text{-}B\text{-}N(O)_s \tag{I}$$

wherein:
    s is an integer equal to 1 or 2, preferably s=2;
    A=R-$T_1$-, wherein
        R is the drug radical and
        $T_1$=(CO)$_t$ or (X)$_{t'}$, wherein X=O, S, $NR_{1C}$, $R_{1C}$ is H or a linear or branched alkyl, having from 1 to 6 carbon atoms, or a free valence, t and t' are integers and equal to zero or 1, with the proviso that t=1 when t'=0; t=0 when t'=1;
    B=-$T_B$-$X_2$—O— wherein
        $T_B$=(CO) when t=0, $T_B$=X when t'=0, X being as above defined;
        $X_2$, bivalent radical, is such that the corresponding precursor of B does not meet test 5 and meets test 4A; said precursor having formula -$T_B$-$X_2$—OH, wherein $T_B$=(CO) and t=0, the free valence of $T_B$ is saturated with:
        —OZ wherein Z=H or $R_{1a}$, $R_{1a}$ being linear or branched when possible $C_1$-$C_{10}$ alkyl, preferably $C_1$-$C_5$, or with -$Z^I$-N-$Z^{II}$, $Z^I$ and $Z^{II}$ being equal or different from each other, having the Z values, when $T_B$=X and t'=0, the free valence of $T_B$ is saturated with H;

with the proviso that:

the drug A=R-$T_1$-, wherein the free valence is saturated as hereinafter mentioned:
    when t'=O with:
        O-Z wherein Z=H or $R_{1a}$ as above defined, or with

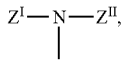

$Z^I$ and $Z^{II}$ being as above defined,
    when t=0 with X-Z, wherein X and Z as above defined, is such as to meet at least one of tests 1-3;
    wherein test 1 (NEM) is a test in vivo carried out on four groups of rats (each formed by 10 rats), the controls (two groups) and the treated (two groups) of which one group of the controls and one group of the treated respectively are administered with one dose of 25 mg/kg s.c. of N-ethylmaleimide (NEM),. the controls being treated with the carrier and the treated groups with the carrier+ the drug of formula A=R-$T_1$- wherein the free valence is saturated as above indicated, administering the drug at a dose equivalent to the maximum one tolerated by the rats that did not receive NEM, i.e. the highest dose administrable to the animal at which there is no manifest toxicity, i.e. such as to be symptomatologically observable; the drug complies with test 1, i.e. the drug can be used to prepare the compounds of general formula (I), when the group of rats treated with NEM+carrier+drug shows gastrointestinal damages, or in the group treated with NEM+carrier+drug are observed gastrointestinal damages greater than those of the group treated with the carrier, or of the group treated with the carrier+drug, or of the group treated with the carrier+NEM;

wherein test 2 (CIP) is a test in vitro wherein human endothelial cells from the umbilical vein are harvested under standard conditions, then divided into two groups (each group replicated five times), of which one is treated with a mixture of the drug $10^{-4}$ M concentration in the culture medium, the other group with the carrier; then cumene hydroperoxide (CIP) having a 5 mM concentration in the culture medium is added to each of the two groups; the drug meets test 2, i.e. the drug can be used to prepare the compounds of general formula (I), if a statistically significant inhibition of the apoptosis (cellular damage) induced by CIP is not obtained with p<0.01 with respect to the group treated with the carrier and CIP;

wherein test 3 (L-NAME) is a test in vivo carried out on four groups of rats (each group formed by 10 rats) for 4 weeks and receiving drinking water, the controls (two groups) and the treated (two groups), of which one group of the controls and of the treated respectively receives in the above 4 weeks drinking water added of N-ω-nitro-L-arginine methyl ester (L-NAME) at a concentration of 400 mg/litre, the controls in the 4 weeks being administered with the carrier and the treated in the 4 weeks with the carrier+the drug, administering the carrier or the drug+carrier once a day, the drug being administered at the maximum dose tolerated by the group of rats not pretreated with L-NAME, i.e., the highest dose administrable to animals at which no manifest toxicity appears, i.e. such as to be symptomatologically observable; after the said 4 weeks, the water supply is stopped for 24 hours and then sacrified, determining the blood pressure 1 hour before sacrifice, and after sacrifice of the rats determining the plasma glutamic pyruvic transaminase (GPT) after sacrifice, and examining the gastric tissue; the drug meets test 3, i.e. the drug can be used to prepare the compounds of general formula (I), when in the group of rats treated with L-NAME+carrier+drug, greater hepatic damages (determined as higher values of GPT) and/or gastric and/or cardiovascular damages (determined as higher values of blood-pressure) are found in comparison respectively with-the group treated with the carrier alone, or with the group treated with the carrier+drug, or with the group treated with the carrier+L-NAME;

wherein test 4A which must be met by the compound precursor of B is a test in vitro wherein a portion of an erythrocyte suspension formerly kept at 4° C. for 4 days, said erythrocytes isolated by standard procedures from Wistar male rats and suspended in a physiological solution buffered at pH 7.4 with phosphate buffer, is centrifuged at 1000 rpm for 5 minutes and 0.1 ml of the centrifuged erythrocytes are diluted with sodium phosphate buffer pH 7.4 at 50 ml; aliquots of 3,5 ml each (No. 5 samples) are taken from said diluted suspension and incubated at 37° C. in the presence of cumene hydroperoxide at a concentration 270 μM and the suspension turbidity determined at 710 nm at intervals of 30 minutes to establish the time (Tmax) at which occurs the maximum turbidity, that corresponds to the maximum amounts of cells lysed by cumene hydroperoxide (haemolysis assumed to be=100%); then alcoholic solutions of the compounds precursors of B are added to 3.5 ml aliquots of the diluted suspension of centrifuged erythrocytes (tests carried out on 5 samples for each precursor of B assayed) in order to have a final concentration 2 mM of the precursor of B and then the resulting suspension preincubated for 30 minutes, cumene hydroperoxide is added in a quantity to have the same above indicated final concentration and at Tmax is determined the percentage of haemolysis inhibition in the sample from the ratio, multiplied by 100, between the absorbance of the sample containing the, erythrocytes, the precursor of B and cumene hydroperoxide respectively and that of the sample containing the erythrocytes and cumene hydroperoxide; the precursors of B meet the test if they inhibit the haemolysis induced by cumene hydroperoxide by a percentage >15%;

wherein test 5 which must not be met by the precursor compound of B is an analytical determination carried out by adding aliquots of $10^{-4}$ M methanol solutions of the precursor of B, to a solution formed by admixing a 2 mM solution of desoxyribose in water with 100 mM of phosphate buffer and 1 mM of the salt $Fe^{II}(NH_4)_2(SO_4)_2$; after having thermostatted the solution at 37° C. for one hour are added, in the order, aliquots of aqueous solutions of trichloroacetic acid 2.8% and of thiobarbituric acid 0.5 M, heating is effected at 100° C. for 15 minutes and the absorbance of the tested solutions is then read at 532 nm; the inhibition induced by the precursor of B in the confront of radical production by $Fe^{II}$ is calculated as a percentage by means of the following formula:

$(1-A_s/A_c) \times 100$ wherein $A_s$ and $A_c$ are respectively the absorbance values of the solution containing the tested compound and the iron salt and that of the solution containing only the iron salt, the compound meets test 5 when the inhibition percentage as above defined of the precursor of B is higher than or equal to 50%; provided that in formula (I) when $X_2$ of B is a linear or branched $C_1$-$C_{20}$ alkylene or a cycloalkylene having from 5 to 7 carbon atoms optionally substituted, the drugs of formula A=R-$T_1$- with the free valence saturated as above described, used in the compound of formula (I), has not to belong to the following classes: drugs for use in incontinence, antithrombotic drugs (ACE inhibitors), prostaglandins, antiinflammatory drugs (NSAIDS and corticosteroids) but not excluding from the antiinflammatory NSAIDS paracetamol and sulindac.

In the formula -$T_B$-$X_2$—O— of the precursor compound of B which meets test 4A and does not meet test 5, compounds wherein $X_2$ is equal to the $R_{1B}$—X—$R_{2B}$ radical wherein $R_{1B}$ and $R_{2B}$, equal to or different from each other, are linear or branched $C_1$-$C_6$ alkylenes, can be used, or $X_2$ is a radical wherein two alkylene chains $C_1$-$C_4$, preferably $C_1$-$C_2$, are linked to non adjacent positions of a central ring having 4 or 6 atoms, preferably 5 or 6 atoms, said ring being an unsaturated cycloaliphatic ring, or a saturated or aromatic eterocyclic ring, containing one or two heteroatoms, equal or different, selected from O, S, N. By unsaturated cycloaliphatic ring it is meant a ring that has not an aromatic character according to the Hückel's rule. Other examples of precursor compounds of B are: 1,4-butandiol: HO—$(CH_2)_4$—OH, 6-hydroxyhexanoic acid: HO—$(CH_2)_5$—COOH, 4-hydroxybutyric acid: HO—$(CH_2)_3$—COOH, N-methyldiethanolamine: HO—

(CH$_2$)$_2$—N(CH$_3$)—(CH$_2$)$_2$—OH, diethylenglycol: HO—(CH$_2$)$_2$—O—(CH$_2$)$_2$—OH, thiodiethylenglycol: HO—(CH$_2$)$_2$—S—(CH$_2$)$_2$—OH; 1,4dioxane-2,6-dimethanol, tetrahydropyrane-2,6-dimethanol, 4H pyrane-2,6-dimethanol, tetrahydrothiopyrane-2,6-dimethanol, 1,4-dithiane-2,6-dimethanol, cyclohexene-1,5-dimethanol, thiazole-2,5-dimethanol, thiophene-2,5-dimethanol, oxazole-2,5-dimethanol, preferably N-methyldiethanolamine, diethylenglycol, thiodiethylenglycol.

The precursor compounds of the drug and of B are prepared according to the known methods in the prior art and described, for example, in "The Merck Index, 12a Ed. (1996), herein incorporated by reference.

The tests conducted to identify the drug corresponding to the R radical of the formula (I) are in detail the following:

Test 1 (NEM): evaluation of the gastrointestinal damage from oxidative stress induced by free radicals formed following administration of N-ethylmaleimide (NEM) (H. G. Utley, F. Bernheim, P. Hochstein "Effects of sulphydril reagents on peroxidation in microsomes" Archiv. Biochem. Biophys. 118, 29-32 1967).

The animals (rats) are distributed in the following groups (no. 10 animals for group):

A) Control Groups:
1° group: treatment: only carrier (aqueous suspension 1% w/v of carboxymethylcellulose, dose: 5 ml/Kg when the drug is administered by os, or a physiologic solution when parenterally administered, i.e. by subcutaneous, intraperitoneal, intravenous or intermuscular route),
2° group: treatment: carrier as above defined+NEM, B) Groups Treated with the Drug:
group I: treatment: carrier+drug,
group II: treatment: carrier+drug+NEM.

The administration routes are those known for the drug, and can be the oral or subcutaneous, intraperitoneal, intravenous or intramuscular route.

The NEM dose is of 25 mg/kg in physiologic solution (sub cutaneous route) and the drug is administered one hour later, in suspension in the carrier, as a single dose which corresponds to the maximum one, or the highest still tolerated by the animals of the group of rats not pretreated with NEM, i.e. the highest administrable dose to said group at which there is no manifest toxicity in the animals, defined as a toxicity that is clearly recognizable for its symtoms. The animals are sacrificed after 24 hours and then one proceeds to the evaluation of the damage to the gastrointestinal mucosa.

The drug meets test 1, i.e. it can be used to prepare the compounds of general formula (I), when the group of rats treated with NEM+carrier+drug shows gastrointestinal damages, or in said group the gastrointestinal damages noticed are greater than those shown by the group treated with the carrier alone, or the group treated with carrier+drug, or the group treated with carrier+NEM, even though the drug pharmacotherapeutic efficacy, assayed by using specific tests, is not significantly reduced.

Test 2 (CIP): Protection parameter of endothelial cell against the oxidative stress induced by cumene hydroperqxide (CIP).

Human endothelial cells of the umbilical vein are prepared according to an usual standard procedure. Fresh umbilical veins are filled with a 0.1% by weight collagenase solution and incubated at 37° C. for 5 minutes.

Afterwards the veins are perfused with medium M 199 (GIBCO, Grand Island, N.Y.) pH 7.4 further added of other substances, as described in the examples. The cells are collected from the perfusate by centrifugation and harvested in culture flasks T-75, pretreated with human fibronectin. The cells are then harvested in the same medium, further added with 10 ng/ml of bovine hypothalamic growth factor. When the cells of the primary cell culture (i.e. that directly obtained from ex-vivo) form a single layer of confluent cells (about 8,000,000 cells/flask), the culture is stopped and the layers washed and trypsinized. The cellular suspensions are transferred into the wells of a cell culture plate having 24 wells, half of which is then additioned with the same culture medium containing the drug at a $10^{-4}$M concentration, and harvested in a thermostat at 37° C. at a constant moisture. Only the cells coming from said first sub-cultures are used for the experiments with cumene hydroperoxide (CIP). The cells are identified as endothelial cells by morphological examination and by their specific immunological reaction towards factor VIII; said cultures did not show any-contaminations from myocytes or fibroblasts.

Before starting the test, the cellular culture medium is removed and the cellular layers are carefully washed with a physiologic solution at a temperature of 37° C. The wells of the culture plate are then incubated for one hour with CIP at a 5 mM concentration in the culture medium. The evaluation of cellular damage (apoptosis) is carried out by determining the percent variation of the DNA fragmentation with respect to the control group (treated with CIP alone), evaluating the fluorescence variation at the wave length of 405-450 nm. 5 replicates for each sample are carried out.

The drug meets the test, i.e. it can be used for preparing the compounds of general formula (I), when a statistically significant inhibition of apoptosis (cellular damage) induced by CIP with respect to the group treated with CIP alone is not obtained at p<0.01.

Test 3 (L-NAME): evaluation of the endothelial dysfunction induced by administration of L-NAME (N$^w$-nitro-L-arginine-methyl ester) J. Clin. Investigation 90, 278-281, 1992.

The endothelial dysfunction is evaluated by determining the damage to the gastrointestinal mucosa, the hepatic damage and blood hypertension induced by administration of L-NAME.

The animals (rats) are divided in groups as herein below shown. The group receiving L-NAME is treated for 4 weeks with said compound dissolved at a concentration of 400 mg/litre in drinking water. The following groups are constituted (No. 10 animals for group):

A) Control Groups:
1° group: only carrier (aqueous suspension 1% w/v of carboxymethylcellulose, dose: 5 ml/Kg when the drug is administered by os, phisiologic solution when administered parenterally),
2° group: carrier+L-NAME, B) Groups Administered with the Drug:
3° group: carrier+drug,
4° group: carrier+drug+L-NAME.

The administration routes are those known for the drug, and can be the oral or subcutaneous, intraperiteneal, intravenous or intramuscular route. The drug is administered at that dose which results the highest still tolerated by the animals of the group of rats not pretreated with L-NAME, i.e. the highest administrable dose at which there is no evident toxicity in the animals, i.e a toxicity recognizable for its symptoms. The drug is administered once a day for 4 weeks.

At the end of the four weeks treatment access to water is prevented and after 24 hours the animals are sacrificed.

One hour before the sacrifice blood-pressure is determined, and a blood pressure increase is taken as an evaluation of the damage to vascular endothelium. The damage to the gastric mucosa is evaluated as illustrated in test 1 (see example F1). The hepatic damage is determined by evaluation of the glutamic-pyruvic transaminase (GPT increase) after sacrifice.

The drug meets test 3, i.e. it can be used for preparing the compounds of general formula (I), when in the group of rats treated with L-NAME+drug+carrier it is found an higher hepatic damage (GPT) and/or an higher gastric damage and/or an higher cardiovascular (blood-pressure) damage in comparison to that of the group treated with the carrier alone, or of the group treated with carrier+drug, or of the group treated with carrier+L-NAME, even if the drug pharmacotherapeutic efficacy, assayed by specific tests, is not significantly reduced.

Under the conditions indicated in the above described in vivo tests 1 and 3 the therapeutic index of the drug is reduced since the usual doses at which the drug can be effective are no longer tolerated.

Test 4A is performed according to the method described by R. Maffei Facino, M Carini G. Aldini, M. T. Calloni, Drugs Exptl. Clin. Res. XXIII (5/8) 157-165 1997. Test 4A is a test in vitro wherein erythrocytes isolated by standard methods from Wister male rats (Charles River), are kept for 4 days at 4° C. in suspension in a physiological solution buffered at pH 7.4 with phosphate buffer. At the end of said period an aliquot of the suspension is taken and centrifuged at 1000 rpm for 5 minutes. 0.1 ml of the centrifuged erythrocytes are diluted to 50 ml with sodium phosphate buffer pH 7.4, obtaining a suspension of erythrocytes 0.2% by volume. No. 5 aliquots of 3.5 ml each of the diluted suspension are added of 0.1-0.3 ml of an alcoholic solution of cumene hydroperoxide in order to have a 270 μM concentration and then incubated at 37° C. This compound causes cell lysis, said lysis causing an increase of turbidity of the suspension. Cell lysis progress is followed by turbidimetry at 710 nm. By performing readings of optical density (or transmittance) at intervals of 30 minutes, it is determined the time (Tmax) at which there is the maximum of turbidity in the suspension, that corresponds to the maximum amount of cells lysed in the suspension. Tmax is assumed to be the time corresponding to 100% of erythrocyte lysis. For determining the inhibiting effect of the precursors of B on haemolysis induced by cumene hydroperoxide, 0.1-0.2 ml of ethanol solutions of each of the assayed compounds precursors of B are added to 3.5 ml aliquots of the suspension of centrifuged erythrocytes (No. 5 samples for each compound) in order to have a 2 mM final concentration, and preincubated for 30 minutes. Cumene hydroperoxide is then added in such a quantity to have the same final previously stated molarity, and the percentage of haemolysis inhibition of the compound at Tmax is determined as the ratio, multiplied by 100, between the absorbance given by the suspension of the sample under assay, containing the erythrocytes, the precursor of B and cumene hydroperoxide respectively, and the absorbance of the suspension containing the erythrocytes and cumene hydroperoxide; the compound pecursor of B meets test 4A if it inhibits the haemolysis induced by cumene hydroperoxide by a percentage >15%;

Test 5 is a colorimetric test wherein 0.1 ml aliquots of $10^{-4}$ M methanolic solutions of the tested products are added to test tubes containing a solution formed by 0.2 ml of 2 mM desoxyribose, 0.4 ml of phosphate buffer pH 7.4 100 mM and 0.1 ml of 1 mM $Fe^{II}(NH_4)_2(SO_4)_2$ in 2 mM HCl. The test tubes are then maintained at 37° C. for one hour. Then in each test tube 0.5 ml of a 2.8% solution in trichloroacetic acid water and 0.5 ml of an aqueous 0.1 M solution of thiobarbituric acid are added, in the order. A reference blank is formed by adding to a test tube containing only the above described aqueous solution of reactants 0.1 ml of methanol. The test tubes are closed and heated in an oil bath at 100° C. for 15 minutes. A pink coloration is developed the intensity of which is proportional to the quantity of desoxyribose undergone to radical oxidative degradation. The solutions are cooled at room temperature and their absorbances are read at 532 nm against the blank. The inhibition induced by the precursor of B or $B_1$ or $C=-T_c-Y-H$ in the confront of radical production by $Fe^{II}$ is determined by means of the following formula:

$$(1-A_s/A_c) \times 100$$

wherein $A_s$ and $A_c$ are respectively the absorbance values of the solution containing the tested compound+the iron salt and that of the solution containing only the iron salt, the compound meets test 5 when the inhibition percentage of radical production as above defined from the precursor of B is higher than or equal to 50%. The compound precursor of B according to the present invention does not meet test 5.

Unexpectedly the invention products of formula (I) have an improved therapeutic index, under oxidative stress conditions, compared with the precursor drugs. The compounds of the invention of formula (I) wherein the compound precursor of B meets test 4A but does not meet test 5 can be used, as above said, as drugs for the therapy of moderate oxidative stress conditions. In this sense according to the present invention, are intended conditions of moderate oxidative stress.

For illustrative purposes the above mentioned tests are referred to the following compounds. See the Tables.

Test 1: Precursor Drug: Indomethacin
  Maximum administrable dose to rats: 7.5 mg/Kg p.o. By administering a higher dose a toxicity is manifested, characterized by enteropathy, tremor, sedation until death (within 24 hours).
  The group of rats treated with NEM+indomethacin at the above mentioned dose shows gastrointestinal damages.
  Since indomethacin in the groups treated with NEM causes gastrointestinal damages, it meets test 1. Indomethacin can therefore be used as a drug for preparing the compounds (I) of the present invention.

Test 2: Precursor Drugs: Indomethacin, Paracetamol and Mesalamine
  Indomethacin and paracetamol meet test 2 since the cellular damage (apoptosis) inhibition induced by CIP is not significantly different with respect to that of the controls.
  Therefore the above drugs can be used as drugs for preparing the compounds (I) of the present invention.
  On the contrary mesalamine does not meet test 2, since it inhibits the apoptosis induced by CIP. Therefore mesalamine according to test 2 could not be used as a precursor to prepare the compounds (I) of the present invention. It has been however found that mesalamine submitted to test 1 causes gastrointestinal damages.
  Thus also mesalamine can be used as a precursor for preparing the compounds (I) of the present invention.

Test 3 (L-NAME) Precurosr Drugs: Paracetamol, Simvastatin, Omeprazole
  Paracetamol and simvastatin meet test 3 since they cause gastric and hepatic damages greater than those induced both by L-NAME+carrier and by the drug+carrier.
  Therefore they can be used as precursors to prepare the compounds (I) of the present invention.
  On the contrary it has been found that omeprazole neither causes gastric nor hepatic damages, nor influences blood-pressure. According to test 3 omeprazole could not be used as a precursor for preparing the compounds (I) of the present invention.

Test 4A (Test for the Precursor of B)

N-methyldiethanolamine shows an inhibition of 54.4% (Table V) of haemolysis induced by cumene hydroperoxide. Therefore it meets test 4A and can be used as precursor of B if it does not meet test 5.

Diethanolamine does not inhibit haemolysis induced by cumene hydroperoxide, and it does not meet test 4A. Therefore this compound cannot be used as precursor of B.

Test 5 (Test for the Precursor of B)

The Table III relating to said test illustrates that N-methyldiethanolamine does not meet test 5, since it does not inhibit radical production from $Fe^{II}$. Therefore it can be used as precursor of B.

The compounds of formula (I) according to the present invention can be transformed into the corresponding salts. For example a method for forming salts is the following. When in the molecule of the formula (I) compounds a nitrogen atom is present sufficiently basic so as to be salified, the corresponding salts of said compounds are obtainable by reaction in organic solvent such as for example acetonitrile, tetrahydrofuran with an equimolecular amount of the corresponding organic or inoganic acid.

Examples of organic acids are: oxalic, tartaric, maleic, succinic, citric acids.

Examples of inorganic acids are: nitric, hydrochloric, sulphuric, phosphoric acids.

The derivatives according to the invention can be used in the therapeutic indications of the precursor drug, allowing to obtain the other advantages exemplified hereinafter for some groups of these drugs:

Anti-inflammatory drugs NSAIDs: the invention compounds result very well tolerated and effective, even when the organism is debilitated and is under conditions of oxidative stress. Said drugs can be used also in those pathologies wherein inflammation plays a significant pathogenetic role, such as for instance, but not limited to, in cancer, asthma, miocardic infarction.

Adrenergic blockers, of α- or β-blocker type: the action spectrum of the compounds of formula (I) results wider than that of the starting drugs: to a direct action on the smooth musculature the inhibition of the nervous beta-adrenergic signals governing the contraction of the hematic ducts is associated. The side effects (dyspnoea, bronchoconstriction) affecting the respiratory apparatus are lower.

Antithrombotic drugs: the antiplatelet activity is potentiated and in the case of the aspirin derivatives the gastric tolerability is improved.

Bronchodilators and drugs active on the cholinergic system: the side effects affecting the cardio-vascular apparatus (tachycardia, hypertension) result lowered.

Expectorants and mucolytic drugs: the gastrointestinal tolerability results improved.

Diphosphonates: the toxicity relating to the gastrointestinal tract is drastically lowered.

Phosphodiesterase (PDE) inhibitors (bronchodilators): the therapeutic efficacy is improved, the dosage being equal; it is therefore possible, using the compounds of the invention to administer a lower dose of the drug and reduce the side effects.

Anti leukotrienic drugs: better efficacy.

ACE inhibitors: better therapeutic efficacy and lower side effects (dyspnoea, cough) affecting the respiratory apparatus.

Antidiabetic drugs (insulin-sensitizing and hypoglycaemizing), antibiotic, antiviral, antitumoral, anticolitic drugs, drugs for the dementia therapy: better efficacy and/or tolerability.

The drugs which can be used as precursors in the general formula of the compounds of the invention are all those meeting at least one of the above mentioned tests 1, 2, 3. Examples of precursor drugs which can be used are the following:

For anti-inflammatory/analgesic drugs, the following can for example be mentioned:

anti-inflammatory drugs: aceclofenac, acemetacin, acetylsalicylic acid, 5-amino-acetylsalicylic acid, alclofenac, alminoprofen, amfenac, bendazac, bermoprofen, α-bisabolol, bromfenac, bromosaligenin, bucloxic acid, butibufen, carprofen, cinmetacin, clidanac, clopirac, diclofenac sodium, diflunisal, ditazol, enfenamic acid, etodolac, etofenamate, felbinac, fenbufen, fenclozic acid, fendosal, fenoprofen, fentiazac, fepradinol, flufenamic acid, flunixin, flunoxaprofen, flurbiprofen, glucametacin, glycol salicylate, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, naproxen, niflumic acid, oxaceprol, oxaprozin, oxyphenbutazone, parsalmide, perisoxal, phenyl acetylsalicylate, olsalazine, pyrazolac, piroxicam, pirprofen, pranoprofen, protizinic acid, salacetamide, salicilamide O-acetic acid, salicylsulphuric acid, salsalate, sulindac, suprofen, suxibuzone, tenoxicam, tiaprofenic acid, tiaramide, tinoridine, tolfenamic acid, tolmetin, tropesin, xenbucin, ximoprofen, zaltoprofen, zomepirac, tomoxiprol; sulindac, differently from other antiinflammatory compounds FANS, is not a cox-inhibitor;

analgesic drugs: acetaminophen (paracetamol), acetaminosalol, aminochlorthenoxazin, acetylsalicylic 2-amino-4-picoline acid, acetylsalicylsalicylic acid, anileridine, benoxaprofen benzylmorphine, 5-bromosalicylic acetate acid, bucetin, buprenorphine, butorphanol, capsaicine, cinchophen, ciramadol, clometacin, clonixin, codeine, desomorphine, dezocine, dihydrocodeine, dihydromorphine, dimepheptanol, dipyrocetyl, eptazocine, ethoxazene, ethylmorphine, eugenol, floctafenine, fosfosal, glafenine, hydrocodone, hydromorphone, hydroxypethidine, ibufenac, p-lactophenetide, levorphanol, meptazinol, metazocine, metopon, morphine, nalbuphine, nicomorphine, norlevorphanol, normorphine, oxycodone, oxymorphone, pentazocine, phenazocine, phenocoll, phenoperidine, phenylbutazone, phenylsalicylate, phenylramidol, salicin, salicylamide, tiorphan, tramadol, diacerein, actarit; paracetamol is not a cox-inhibitor;

for respiratory and urogenital apparatus drugs (bronchodilators and drugs active on the cholinergic system, expectorants/mucolytics, antiasthmatic/antiallergic antihistaminic drugs), the following can be mentioned:

bronchodilators and drugs active on the cholinergic system: acefylline, albuterol, bambuterol, bamifhylline, bevonium methyl sulphate, bitolterol, carbuterol, clenbuterol, chlorprenaline, dioxethedrine, difylline, ephedrine, epinephrine, eprozinol, etafredine, ethylnorepinephrine, etofylline, fenoterol, flutoprium bromide, hexoprenaline, ipratropium bromide, isoetharine, isoprotenerol, mabuterol, metaproterenol, oxybutynin, oxitropium bromide, pirbuterol, procaterol, protokylol, proxyphylline, reproterol, rimiterol, salmeterol, soterenol, terbutaline, 1-teobromineacetic acid, tiotropium bromide, tretoquinol, tulobuterol, zaprinast, cyclodrine, NS-21, 2-hydroxy-2,2-diphenyl-N-(1,2,3,6-tetrahydro-pyridin-4-ylmethyl)acetamide;

expectorant/mucolytic drugs: acetil-cysteine, ambroxol, bromhexine, carbocysteine, domiodol, erdosteine, ferulic acid, guaiacol, guaifenesin, iodinated glycerol, letosteine, mecysteine hydrochloride, mesna, sobrerol, stepronin, terpin, tiopronin;

antiasthmatic/antiallergic antihistaminic drugs: acrivastine, alloclamide, amlexanox, cetirizine, clobenzepam, chromoglycate, chromolyn, epinastine, fexofenadine, formoterol, histamine, hydroxyzine, levocabastine, lodoxamide, mabuterol, metron s, montelukast, nedocromil, repirinast, seratrodast, suplatast tosylate, terfenadine, tiaramide, urushiol, bromhexine;

for cardiovascular drugs (ACE-inhibitors, beta-blockers, antithrombotic and vasodilator drugs, antidiabetic and hypoglycemic drugs), the following can be mentioned:

ACE-inhibitors: alacepril, benazepril, captopril, ceronapril, cilazapril, delapril, enalapril, enalaprilat, fosinopril, imidapril, lisinopril, losartan, moveltipril, naphthopidil, perindopril, quinapril, ramipril, spirapril, temocapril, trandolapril, urapidil;

beta-blockers: acebutolol, alprenolol, amosulalol, arotinolol, atenolol, betaxolol, bevantolol, bucumolol, bufetolol, bufuralol, bunitrolol, bupranolol, butofilol, carazolol, carteolol, carvedilol, celiprolol, cetamolol, dilevalol, epanolol, esmolol, indenolol, labetalol, mepindolol, metipranolol, metoprolol, moprolol, nadolol, nadoxolol, nebivolol, nifenalol, nipridalol, oxprenolol, penbutolol, pindolol, practolol, pronethalol, propranolol, sotalol, sulfinalol, talinolol, tertatolol, tilisolol, timolol, toliprolol, xibenolol;

antithrombotic and vasoactive drugs: acetorphan, acetylsalicylic acid, argatroban, bamethan, benfurodil hemisuccinate, benziodarone, betahistine, brovincamine, bufeniode, citicoline, clobenfurol, clopidogrel, cyclandelate, dalteparin, dipyridamole, droprenilamine, enoxaparin, fendiline, ifenprodil, iloprost, indobufen, isbogrel, isoxsuprine, heparin, lamifiban, midrodine, nadroparin, nicotinyl alcohol, nylidrin, ozagrel, perhexiline, phenylpropanolamine, prenylamine, papaveroline, reviparin salt, ridogrel, suloctidil, tinofedrine, tinzaparin, trifusal, xanthinol niacinate;

antidiabetic drugs: acarbose, carbutamide, glibornuride glybuthiazol(e), miglitol, repaglinide, troglitazone, 1-butyl-3-metanyl-urea, tolrestat, nicotinamide;

for antitumoral drugs, the following can be mentioned: ancitabine, anthramycin, azacitidine, azaserine, 6-azauridine, bicalutamide, carubicin, carzinophilin, chlorambucil, chlorozotocin, cytarabine, daunorubicin, defosfamide, demecolcine, denopterin, 6-diazo-5-oxo-L-norleucine, docetaxel, doxifluridine, doxorubicin, droloxifene, edatrexate, eflornithine, enocitabine, epirubicin, epitiostanol, etanidazole, etoposide, fenretinide, fludarabine, fluorouracil, gemcitabine, hexestrol, idarubicin, lonidamine, mannomustine, melphalan, menogaril, 6-mercaptopurine, methotrexate, mitobronitol, mitolactol, mitomycins, mitoxantrone, mopidamol, mycophenolic acid, ninopterin, nogalamycin, paclitaxel, pentostatin, pirarubicin, piritrexim, plicamycin, podophyllic acid, porfimer sodium, porfiromycin, propagermanium, puromycin, ranimustine, retinoic acid, roquinimex, streptonigrin, streptozocin, teniposide, tenuazonic acid, thiamiprine, thioguanine, tomudex, topotecan, trimetrexate, tubercidin, ubenimex, vinblastine, vincristine, vindesine, vinorelbine, zorubicin;

for antiulcer drugs the following can be mentioned: acetamidocaproic acid, arbaprostil, cetraxate, cimetidine, ecabet, enprostil, esaprazole, irsogladine, misoprostol, omeprazole, ornoprostil, pantoprazole, plaunotol, rioprostil, rosaprostol, rotraxate, sofalcone, trimoprostil;

among anti-hyperlipidemic drugs (statines) the following can be mentioned: atorvastatin, cilastatin, dermostatin, fluvastatin, lovastatin, mevastatin, nystatin, pentostatin, pepstatin, privastatin sodium, simvastatin;

among antibiotic/antiviral drugs the following can be mentioned:

antibiotics: amdinocillin, amoxicillin, ampicillin, apalcillin, apicycline, aspoxicillin, azidamfenicol, azidocillin, azlocillin, aztreonam, benzoylpas, benzyl penicillinic acid, biapenem, bicozamycin, capreomycin, carbenicillin, carindacillin, carumonam, cefaclor, cefadroxil, cefamandole, cefatrizine, cefazedone, cefazolin, cefbuperazone, cefclidin, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefoxitin, cefozopran, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, chloramphenicol, chlortetracycline, cinoxacin, clavulanic acid, clometocillin, cloxacillin, cyclacillin, cycloserine, demeclocycline, dicloxacillin, epicillin, fenbecillin, flomoxef, floxacillin, hetacillie, imipenem, lenampicillin, loracarbef, lymecycline, mafenide, meclocycline, meropenem, metampicillin, methacycline, methicillin sodium, mezlocillin, minocycline, moxalactam, mupirocin, myxin, negamycin, riovobiocin, oxacillin, panipenem, penicillin G potassium salt, penicillin N, penicillin O, penicillin V, phenethicillin potassium salt, pipacycline, piperacillin, pirlimycin, porfiromycine, propicillin, quinacillin, ritipenem, rolitetracycline, sancycline, sedecamycine, spectinomycin, sulbactam, sulbenicillin, temocillin, tetracycline, ticarcillin, tigemonam, tubercidin, azithromycin, clarithromycin, dirithromycin, enviomycin, erythromycin, josamycin, midecamycin, miokamycin, oleandomycin, rifabutin, rifamide, rifamycin, rifaximin, rokitamycin, spiramycin, troleandromycin, viomycin, virginiamycin;

amikacin, apramycin, arbekacin, dibekacin, dihydrostreptomycin, fortimicins, gentamicin, micronomicin, neomycin, netilmicin, paromomycin, ribostamycin, sisomicin, spectinomycin, streptomicin, tobramycin, trospectomycin;

bacampicillin, cefcapene pivoxil, cefpodoxime proxetil, panipenem, pivampicillin, pivcefalexin, sultamicillin, talampicillin;

carbomycin, clindamycin, lincomycin, mikamycin, rosaramicin, ciprofloxacin, clinafloxacin, difloxacin, enoxacin, enrofloxacin, fleroxacin, flumequine, grepafloxacin, lomefloxacin, nadifloxacin, nalidixic acid, norfloxacin, ofloxacin, pazufloxacin, pefloxacin, pipemidic acid, piromidic acid, rufloxacin, sparfloxacin, tosufloxacin, trovafloxacin, clomocycline, guamecycline, oxytetracycline, nifurpirinol, nifurprazine; p-aminosalicylic acid, p-aminosalicylic acid hydrazide, clofazimine, deoxydihydrostreptomycin, ethambutol, glyconiazide, isoniazid, opiniazide, phenyl aminosalicylate, rifampin, rifapentine, salinazid, 4-4'-sulfynyldianiline, Acediasulfone, dapsone, succisulfone, p-sulfanilylbenzylamine, thiazolsulfone, acetyl sulfamethoxypyrazine, mafenide, 4'-(methylsulfamoyl)sulfanilanilide, salazosulfadimidine, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanole, sulfalene, sulfamerazine, sulfameter, sulfamethazine, sulfamethizole, sulfamethomidine, sulfamethoxazole, sulfamethoxypyridazine, sulfamethylthiazole, sulfametrole, sulfamidochrysoidine, sulfamoxole, sulfanilamide, 2-p-sulfanilylanilinoethanol, N⁴-sulfanilylsulfanilamide, sulfanilylurea, N-sulfanilyl-3,4-xylamide, sulfaperine, sulfaphenazole, sulfaproxyline, sulfapyrazine, sulfapyridine, sulfasomizole, sulfasymazine, sulfathiazole, sulfathiourea, sulfisomidine, sulfisoxazole, 4-sulfanilamido salicylic acid; negamycin, carumonan, cloxyquin, nitroxoline, arginine, metronidazole;

antiviral drugs: acyclovir, amantadine, cidofovir, cytarabine, didanosine, dideoxyadenosine, edoxudine, famciclovir, floxuridine, ganciclovir, idoxuridine, indanavir, kethoxal, lamivudine, MADU, penciclovir, podophyllotoxin, ribavirin, rimantadine, saquinavir, sorivudine, stavudine, trifluridine, valacyclovir, vidarabine, xenazoic acid, zalcitabine, zidovudine;

among the bone resorption inhibitors (diphosphonates) the following can be mentioned: alendronic acid, butedronic acid, etidronic acid, oxidronic acid, pamidronic acid, risedronic acid;

among antidementia drugs the following can be mentioned: amiridine, lazabemide, mofegiline, salbeluzol, oxiracetam, ipidacrine, nebracetam, tacrine, velnacrine.

The preferred substances are the following:

among anti-inflammatories: acetylsalicylic acid, 5-aminoacetylsalicylic acid, carprofen, diclofenac sodium, diflunisal, etodolac, flufenamic acid, flunixin, flurbiprofen, ibuprofen, indomethacin, indoprofen, ketoprofen, ketorolac, lornoxicam, loxoprofen, meclofenamic acid, mefenamic acid, meloxicam, mesalamine, naproxen, niflumic acid, olsalazine, piroxicam, salsalate, sulindac, suprofen, tenoxicam, tiaprofenic acid, tolfenamic acid, tolmetin, zomepirac, tomoxiprol;

among analgesic drugs: acetaminophen, acetylsalicylsalicylic acid, benoxaprofen, buprenorphine, butorphanol, capsaicin, diacereine, dihydrocodeine, ethylmorphine, eugenol, phenylbutazone, meptazinol, morphine, nalbuphine, pentazocine, thiorphan, tramadol, actarit;

among respiratory and urogenital apparatus drugs: (bronchodilators, drugs active on the cholinergic system, expectorants/mucolytics, antiasthmatics/antiallergic antihistaminic drugs):

bronchodilators and drugs active on the cholinergic system: albuterol, carbuterol, clenbuterol, diphylline, etophylline, fenoterol, ipratropium bromide, metaproterenol, oxybutynin, pirbuterol, salmeterol, terbutaline, tiotropium bromide, zaprinast, cyclodrine, NS-21, 2-hydroxy-2,2-diphenyl-N-(1, 2,3,6-tetrahydro-pyridin-4-ylmethyl)acetamide;

expectorant/mucolytic drugs: acetyl-cysteine, ambroxol, bromexine, carbocysteine, guaiacol, ferulic acid, mecysteine hydrochloride, sobrerol;

antiasthmatic/antiallergic antihistaminic drugs: cetirizine, chromoglycate, histamine, levocabastine, lodoxamide, montelukast, terfenadine, bromhexine.

Among cardiovascular drugs:

ACE-inhibitors: captopril, enalapril, lisinopril, losartan, ramipril;

beta blockers: alprenolol, atenolol, bupranolol, labetalol, metipranolol, metoprolol, pindolol, propranolol, timolol;

antithrombotic and vasoactive drugs: acetylsalicylic acid, acetorphan, argatroban, clopidogrel, dalteparin, dipyridamole, enoxaparin, heparin, iloprost, midodrine, ozagrel, phenylpropanolamine trifusal;

antidiabetic drugs: tolrestat, nicotinamide;

among antitumoral drugs: anthramycin, daunorubicin, doxorubicin, epirubicin, fluorouracil, methotrexate, vinblastine;

among antiulcer drugs: cimetidine, omeprazole, pantoprazole;

among antihyperlipidemic drugs: lovastatin, pravastatin sodium, simvastatin;

Among antibiotic/antiviral drugs:

antibiotic drugs: amoxicillin, ampicillin, aztreonam, biapenem, carbenecillin, cefaclor, cefadroxil, cefamandole, cefatrizine, cefoxitin, clavulanic acid, dicloxacillin, imipenem, meclocycline, methacycline, moxalactam, panipenem, sulbactam, azithromycin, erythromycin, josamycin, miokamycin, rifabutine, rifamide, rifamycin, gentamicin, paromomycin, sisomicin, bacampicillin, carbomycin, clindamycin, ciprofloxacin, clinafloxacin, difloxacin, enrofloxacin, lomefloxacin, nadifloxacin, norfloxacin, ofloxacin, pipemidic acid, apicycline, clomocycline, oxytetracycline, nifurpirinol, nifurprazine, isoniazid, rifampin, rifapentine, dapsone, thiazolsulfone, sulfamethoxazole, sulfamoxole, metronidazole, arginine;

antiviral drugs: acyclovir, famciclovir, ganciclovir, penciclovir, ribavirin, vidarabine, zidovudine;

among the bone resorption inhibitors: alendronic acid, etidronic acid, pamidronic acid;

among antidementia drugs: oxiracetam, tacrine, velnacrine.

The above mentioned substances, R precursors, are prepared according to the methods known in the prior art. See for example in "The Merck Index, 12a Ed. (1996), herein incorporated by reference. When available, the corresponding isomers, comprising optical isomers, can be used.

Tomoxiprol is obtained according to the method described in EP 12,866.

When in the compounds of formula (I) the precursor drug is a steroid, A=R— having the following structure:

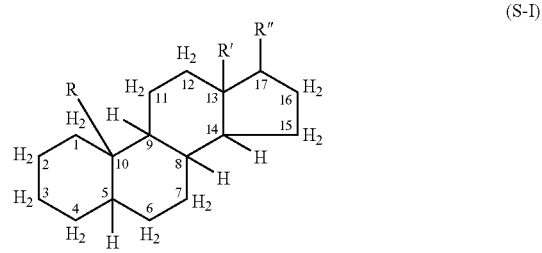

(S-I)

wherein in substitution of the hydrogens of the CH groups or of the two hydrogens of the $CH_2$ groups mentioned in the general formula, the following substituents can be present:

in position 1-2: there may be a double bond;

in position 2-3: there may be the following substituent:

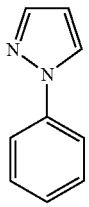
(S-II)

in position 2: there may be Cl, Br;
in position 3: there may be CO, —O—$CH_2$—$CH_2$—Cl, OH;
in position 3-4: there may be a double bond;
in position 4-5: there may be a double bond;
in position 5-6: there may be a double bond;
in position 5-10: there may be a double bond;
in position 6: there may be Cl, F, $CH_3$, —CHO;
in position 7: there may be Cl, OH;
in position 9: thre may be Cl, F;
in position 11: there may be OH, CO, Cl, $CH_3$;
in position 16: there may be $CH_3$, OH, =$CH_2$:
in position 17: there may be OH, $CH_3$, OCO(O)$_{ua}$($CH_2$)$_{va}$$CH_3$, C≡CH or

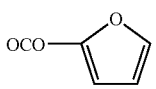
(S-III)

wherein ua is an integer equal to 0 or 1, va is an integer from 0 to 4;
in position 16-17: there may be the following groups:

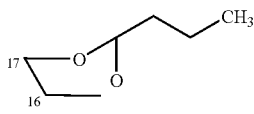
(S-IVa)

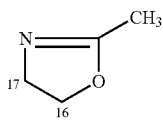
(S-IVb)

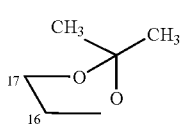
(S-IVc)

R and R', equal to or different from each other, can be hydrogen or linear or branched alkyls from 1 to 4 carbon atoms, preferably R=R'=$CH_3$;

R" is —(CO-L)$_t$-(L)$_{t2}$-($X_O^I$)$_{t1}$— wherein t, t1 and t2 are integers equal to or different from each other, equal to 0 or 1, with the proviso that when t=0 t2=1 and when t=1 t2=0, and that t and t1, or t2 and t1, cannot contemporaneously be equal to 0 when A does not contain —OH groups;

the bivalent bridging group L is selected from:

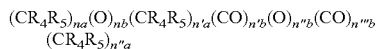

wherein na, n'a, and n"a, equal to or different from each other, are integers from 0 to 6, preferably 1-3; nb, n'b, n"b and n'''b, equal to or different from each other, are integers equal to 0 or 1; $R_4$, $R_5$, equal to or different from each other, are selected from H, linear or branched alkyl from 1 to 5 carbon atoms, preferably from 1 to 3;
$X_O^I$ is X as above defined, or equal to $X_2^I$ wherein $X_2^I$ is equal to OH, $CH_3$, Cl, N(—$CH_2$—$CH_3$)$_2$, $SCH_2F$, SH, or

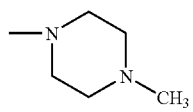
(s-v)

Preferably R" in the formula (S—I) is —CO—$CH_2OH$, or —CH($CH_3$)—$CH_2$—$CH_2$—COOH.

In the precursor steroids those having the hydroxyl function in position 3 and/or in position 11, and/or having in R" an hydroxyl or carboxylic function in terminal position, are preferred.

The precursor steroids of A which can be mentioned and which are preferred, are those listed herein under, obtainable according to the processes known in the prior art.

As precursors and respective processes, those for example described in The Merck Index, ed. 12 of 1996, herein incorporated by reference, can be mentioned. The precursors (according to the Merck nomenclature) are the following, wherein $H_2$, H, R, R', R' have the meaning mentioned in the compounds listed herein: Budesonide, Hydrocortisone, Alclomethasone, Algestone, Beclomethasone, Betamethasone, Chloroprednisone, Clobetasol, Clobetasone, Clocortolone, Cloprednol, Cortisone, Corticosterone, Deflazacort, Desonide, Desoximethasone, Dexamethasone, Diflorasone Diflucortolone, Difluprednate, Fluazacort, Flucloronide, Flumethasone, Flunisolide, Fluocinolone Acetonide, Fluocinonide, Fluocortyn Butyl, Fluocortolone, Fluorometholone, Fluperolone Acetate, Fluprednidene Acetate, Fluprednisolone, Flurandrenolide, Formocortal, Halcinonide, Halobetasol Propionate, Halomethasone, Halopredone Acetate, Hydrocortamate, Loteprednol Etabonate, Medrysone, Meprednisone, Methylprednisolone, Mometasone Furoate, Paramethasone, Prednicarbate, Prednisolone, Prednisolone 25-Diethylaminoacetate, Prednisolone Sodium Phosphate, Prednisone, Prednival, Prednylidene, Rimexolone, Triamcinolone, Triamcinolone, Acetonide, 21-Acetoxypregnenolone, Cortivazol, Amcinonide, Fluticasone Propionate, Mazipredone, Tixocortol, Triamcinolone Hexacetonide, Ursodesoxycholic acid, Chenodeoxycholic acid, Mitatrienediol, Moxestrol, Ethynylestradiol, Estradiol, Mestranol.

The efficacy of the compounds according to the present invention as drugs to be used in the conditions of moderate oxidative stress has been shown also in a pharmacological test in which said compounds have been able to inhibit the cytolesive effects induced by hydrogen peroxide on human endothelial cells of the umbilical vein. The endothelial cell is one of the first cell hit in pathological processes ("Pathophysiology: the biological basis for disease in adults and children" by McCance & Huether, 1998, page 1025) and the hydrogen peroxide is a mild oxidant and is considered as an essential mediator agent in pathologies connected to oxidative stress (B. Halliwell, J. Gutteridge "Free Radicals in Biology and Medicine", page 416, 1993). The effectiveness to neutralize their cytolesive effects is considered essential for the pharmacological activity of compounds to be used under oxidative stress conditions (B. Halliwell, J. Gutteridge "Free Radicals in Biology and Medicine", page 416, 1993).

The compounds of formula (I) are prepared by means of the reactions specified below.

If the reactive function of the drug (for example —COOH, —OH) is involved in a covalent bond, for example of ester, amide, ether type, said function, before carrying out the preparation of the mentioned compounds, can be restored with the methods well known in the prior art.

The reactions used for obtaining the compounds of formula (I) are reactions leading to the formation of bonds for example of ester, amide, thioester type well known to the skilled in the field.

When in the two reaction compounds other functional groups COOH and/or HX, wherein X is as above defined, are present, they must be protected before the reaction according to the methods known in the prior art; for example as described in the publication by Th. W. Greene: "Protective groups in organic synthesis", Harward University Press, 1980.

The compounds of formula I wherein s=2 are prepared as mentioned hereinafter.

IA)—The drug has general formula R—COOH and the functional group of the precursor compound of B which links itself to the drug carboxylic function has formula XZ, X being as above defined and Z=H, an OH function or an halogen atom being also contemporaneously present in the precursor compound of B as reactive groups for the nitration reaction.

The general synthesis scheme, if in the precursor compound of B also an OH function is present, implies the initial formation of the R—COHal acid halide (Hal=Cl, Br) and the subsequent reaction with the HX group of the precursor compound of B:

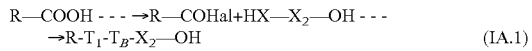

(IA.1)

wherein $X_2$, $T_1$, $T_B$ are as above defined.

The RCOHal acylhalide is prepared according to the methods known in the prior art, for example by thionyl or oxalyl chloride, or by $P^{III}$ or $P^V$ halides in inert solvents under the reaction conditions, such as for example toluene, chloroform, DMF, etc. Then the acyl halide is reacted with the group HX of the precursor of B by using an inert solvent under the reaction conditions such as toluene, tetrahydrofuran, chloroform, etc. at a temperature in the range 0° C.-25° C.

Alternatively to the previous synthesis, the precursor drug of formula R—COOH can be treated with an agent activating the carboxyl group selected from N,N'-carbonyldiimidazol (CDI), N,N'-dicyclohexylcarbodiimide in an inert solvent under the reaction conditions such as toluene, tetrahydrofuran, chloroform, etc. at a temperature in the range −5° C. and +50° C. The obtained compound is reacted in situ with the precursor of B, after the OH function present in the precursor of B has been protected, for example by formation of an acetyl group, recovering the initial function at the end of the synthesis by the methods well known in the prior art. The reaction scheme is the following:

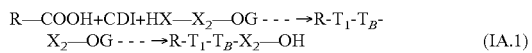

(IA.1)

wherein $X_2$, $T_1$, $T_B$ are as above defined and G is a protective group of the OH function.

The compound of formula (IA.1) is then subjected to halogenation reaction, for example by $PBr_3$, $PCl_5$, $SOCl_2$, $PPh_3$, and $I_2$ in an inert solvent under the reaction conditions such as toluene, tetrahydrofuran, chloroform, etc. at a temperature in the range −5° C. and +50° C. The halogen derivative is reacted with $AgNO_3$ in organic solvent such as acetonitrile, tetrahydrofuran at a temperature in the range 25° C.-80° C. The reaction scheme is the following:

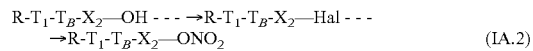

(IA.2)

Alternatively, when $X_2$ is a linear $C_4$ alkyl, the R—COOH acid is reacted with triphenylphosphine in the presence of an halogenating agent such as $CBr_4$ or N-bromosuccinimide in tetrahydrofuran and the resulting compound (IA.2), wherein $X_2$ is butylene, is nitrated as above mentioned.

Or it is possible to convert the R—COOH acid into its sodic salt, by using methods known in the prior art, and reacting it with an halogen derivative of formula Hal-$X_2$—$R_3$ wherein $R_3$ is OH, Hal in an inert solvent under the reaction conditions such as tetrahydrofuran, chloroform, etc. at a temperature in the range −5° C. and +25° C. If $R_3$=Hal the obtained derivative is nitrated as above mentioned. The reaction scheme is the following:

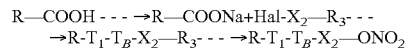

IIA)—The drug has general formula R—XH and the functional group of the precursor compound of B which links itself to the function HX of the drug is a carboxylic group, X being as above defined, an OH function or an halogen atom being also contemporaneously present in the precursor compound of B as reactive groups for the nitration reaction.

The general synthesis scheme implies the reaction of the acid HOOC—$X_2$—$R_4$ wherein $R_4$ is Hal, OG wherein G is a suitable protecting group, with an activating agent as mentioned in IA) and the subsequent reaction with the HX group of the drug.

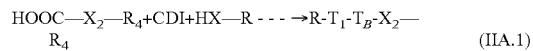

(IIA.1)

wherein $X_2$, $T_1$, $T_B$, $R_4$ are as above defined.

The obtained compound (IIA.1) is transformed into the corresponding nitroderivative as mentioned in IA). If the substituent OG is present, the protecting group is first removed by the known methods.

Alternatively to the previous synthesis, the drug R—OH is reacted with an acyl halide having formula Hal-$X_2$—COHal according to the conditions mentioned in IA) and the obtained halogen derivative is then nitrated as above mentioned:

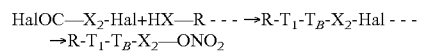

wherein $X_2$, $T_1$, $T_B$ are as above defined.

The compounds of formula I wherein s=1 are prepared as mentioned hereinafter.

IB)—The drug has general formula R—COOH and the functional group of the precursor compound of B which links itself to the drug carboxylic function has formula XZ, X being as above defined and Z=H, the precursor compound of B containing also an hydroxyl function or an halogen atom as reactive groups for the nitration reaction.

The compound of formula R-$T_1$-$T_B$-$X_2$—OH (IA.1) obtained as reported in IA) is transformed into nitroso derivative by reaction with sodium nitrite in water in the presence of hydrochloric acid, according to the procedures known in the prior art.

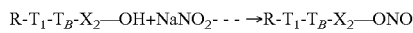

IIB)—The drug has general formula R—XH and the functional group of the precursor compound of B which links itself to the function HX of the drug is a carboxylic group, X being as above defined. The synthesis scheme is similar to that described in IIA).

The compound of formula $R-T_1-T_B-X_2-R_4$ (IIA.1), obtained as reported in IIA) is transformed into the nitroso derivative as mentioned in IB).

The compounds of the present invention are formulated in the corresponding pharmaceutical compositions for parenteral, oral and topic use according to the methods well known in the prior art, together with the usual excipients; see for example the publication "Remington's Pharmaceutical Sciences 15a Ed."

The amount on molar basis of the active principle in these formulations is the same, or lower, in comparison with that used of the corresponding precursor drug.

The daily administrable doses are those of precursor drugs, or in the case lower. The daily doses can be found in the publications of the field, such as for example in "Physician's Desk reference".

The following examples have the purpose to illustrate the invention and are not to be considered as limitative of the same.

EXAMPLE 1

Preparation of 4-nitroxybutyric acid 4'-acetylamino phenyl ester

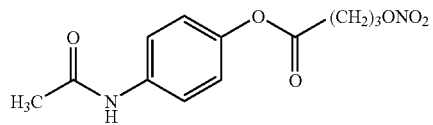

(E-1)

The drug is paracetamol of formula

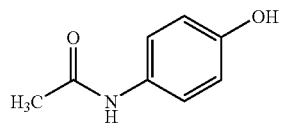

(E-1a)

The precursor compound of B is the 4-hydroxybutyric acid.

a) Preparation of 4-bromobutyric acid 4'-actylamino phenyl ester

To a solution of 4-bromobutyric acid (4.6 g, 27.6 mmoles) in chloroform (45 ml) and N,N-dimethylformamide (20 ml), paracetamol (4.17 g, 27.6 mmoles), N,N'-dicyclohexyl carbodiimide (8.42 g, 40.8 mmoles) and 4-dimethyl aminopyridine (0.15 g, 1.25 mmoles) are added. The reaction mixture is maintained under stirring at room temperature for 72 hours, filtered and evaporated under vacuum. The reaction crude material is treated with ethyl acetate and washed with brine and then with water. The organic phase is anhydrified with sodium sulphate and then evaporated under vacuum. The residue is purified by chromatogrphy on silica gel eluting with n-hexane/ethyl acetate 4/6 (ratio V/V). 5.33 g of the product are obtained as a white solid. M.p.=108°-110° C.

b) Preparation of 4-nitroxybutyric acid 4'-acetylamino phenylester

To a solution of 4-bromobutyric acid 4'-acetyl amino phenyl ester (5.33 g, 17.8 mmoles) in acetonitrile (80 ml) silver nitrate (4.56 g, 26.9 mmoles) is added. The reaction mixture is heated for 16 hours away from light at 80° C., then cooled to room temperature, filtered to remove the silver salts, and evaporated under reduced pressure. The residue is purged by chromatography on silica gel eluting with n-hexane/ethyl acetate 4/6. 4.1 g of the product are obtained as a white solid. M.P.=80-83° C.

| Elementary analysis: | C | H | N |
|---|---|---|---|
| Calculated | 51.07% | 4.99% | 9.92% |
| Found | 51.06% | 5.00% | 9.90% |

EXAMPLE 2

Preparation of 4-hydroxy-3-(4-nitroxybutanoyloxymethyl)-α-[(tertbutylamino)methyl]benzyl alcohol

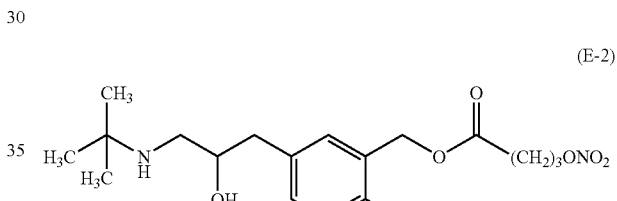

(E-2)

The precursor drug is salbutamol of formula

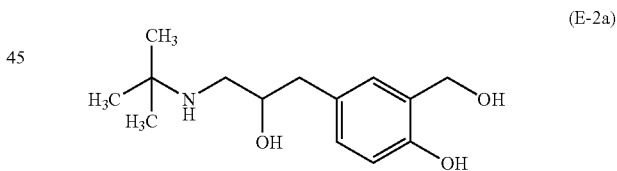

(E-2a)

The precursor compound of B is the 4-hydroxybutyric acid.

The compound (E-2) is synthetized according to the procedure described in Example 1. Yield: 21%.

| Elementary analysis: | C | H | N |
|---|---|---|---|
| Calculated | 55.13% | 7.07% | 7.56% |
| Found | 55.10% | 7.09% | 7.57%. |

EXAMPLE 3

Preparation of 4-(nitroxy)butyric acid 4-[(2-amino-3,5-dibromophenyl)methylamino]trans cyclohexyl ester

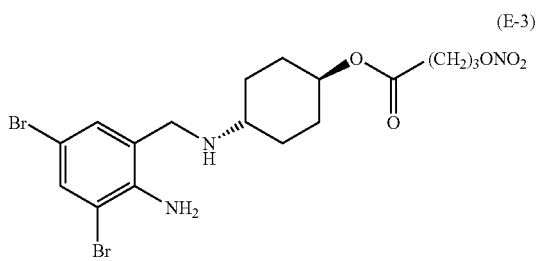

(E-3)

The precursor drug is ambroxol

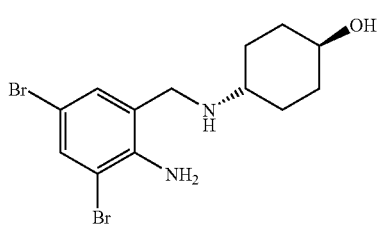

(E-3a)

The precursor compound of A is the 4-hydroxybutyric acid.

a) Preparation of 4-[(2-tert-butoxycarbonylamino-3,5-dibromophenyl)methylamino]trans cyclohexanol To a solution of ambroxol (5 g, 13.22 mmoles) in dioxane (35 ml) and water (50 ml), triethylamine (3.31 ml, 23.7 mmoles) and di-tert-butyldicarbonate (3.46 g, 15.86 mmoles) are added. The reaction mixture is left under stirring at room temperature for 24 hours, then concentrated at reduced pressure. The residue is treated by adding portions of a 1% HCl solution until pH 7, then the solution is extracted with ethyl acetate. The organic phase anhydrified with sodium sulphate is evaporated under vacuum. 4-[(2-tert-butoxycarbonylamino-3,5-dibromophenyl)methylamino]trans cyclohexanol is obtained, which is used in the subsequent step without further purification.

b) Preparation of 4-(nitroxy)butyric acid 4-[(2-tert-butoxycarbonylamino-3,5-dibromophenyl)methylamino]trans cyclohexyl ester The compound is synthetized according to the procedure described in Example 1. Yield 57%.

c) Preparation of 4-(nitroxy)butyric acid 4-[(2-amino-3,5-dibromophenyl)methylamino]trans cyclohexyl ester To a solution of 4-(nitroxy)butyric acid 4-[(2-tert-butoxycarbonylamino-3,5-dibromophenyl)methylamino]trans cyclohexyl ester (3.5 g, 5.74 mmoles) in ethyl acetate (100 ml), cooled at 0° C., a 5N HCl solution in ethyl acetate (5.95 ml) is added. The solution is maintained under stirring at 0° C. for 5 hours, then filtered. The obtained solid is suspended in ethyl acetate and the organic layer washed with a 5% sodium carbonate solution. The organic phase is washed with water, anhydrified with sodium sulphate and evaporated at reduced pressure. The residue is purified by chromatography on silica gel, eluting with n-hexane/ethyl acetate 1/1 (ratio by volume). 4-(nitroxy)butyric acid 4-[(2-amino-3,5-dibromophenyl)methylamino]trans cyclohexyl ester is obtained. Yield 31%.

| Elementary analysis: | C | H | N | Br |
|---|---|---|---|---|
| Calculated | 40.10% | 4.55% | 8.25% | 31.38 |
| Found | 40.07% | 4.54% | 8.26% | 31.39% |

EXAMPLE 4

Preparation of [4-[4-(nitroxy)butyroyl]amino-1-hydroxybutylidene]biphosphonic acid

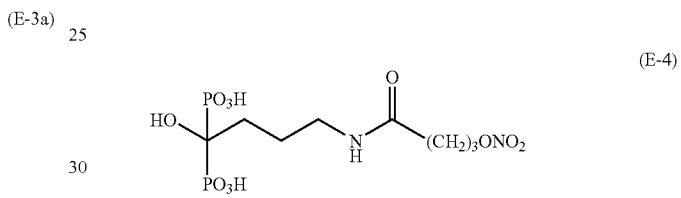

(E-4)

The precursor drug is alendronic acid of formula

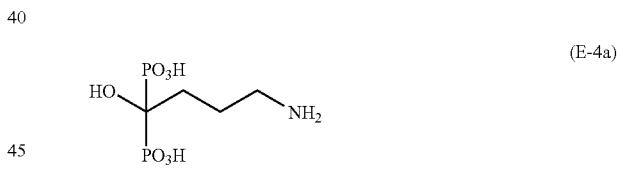

(E-4a)

The precursor compound of B is 4-hydroxybutyric acid.

The compound is synthetized according to the procedure described in Example 1. Yield: 11%.

| Elementary analysis: | C | H | N |
|---|---|---|---|
| Calculated | 25.27% | 4.77% | 7.37% |
| Found | 25.26% | 4.79% | 7.37%. |

EXAMPLE 5

Preparation of [2-[4-[(4-chlorophenyl)phenylmethyl]1-piperazinyl]ethoxy]acetic acid [N-methyl-N-(2-nitroxyethyl)]-2-aminoethyl ester

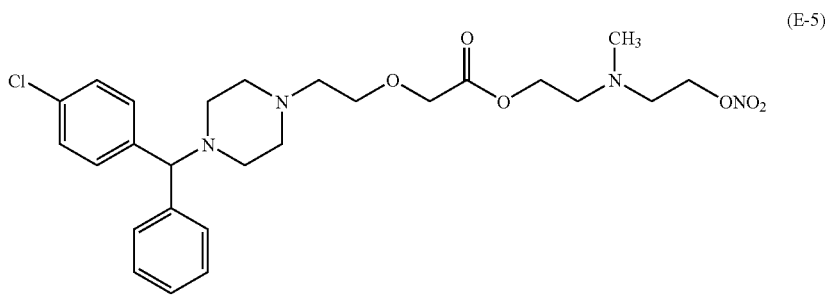
(E-5)

The precursor drug is cetirizine

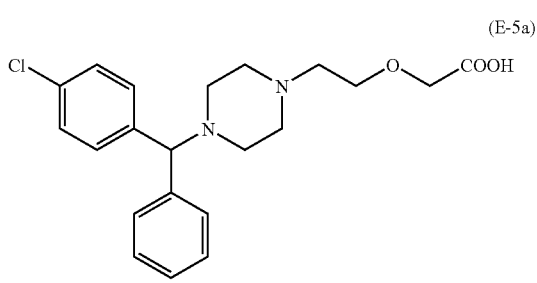
(E-5a)

The precursor compound of B is N-methyldiethanolamine of formula HO—$(CH_2)_2$—$N(CH_3)$—$(CH_2)_2$—OH.

a) Preparation of [2-[4-[(4-chlorophenyl)phenylmethyl]1-piperazinyl]ethoxy]acetic acid [N-methyl-N-(2-hydroxyethyl)]-2-aminoethyl ester To a solution of cetirizine (5 g, 12.85 mmoles) in N,N-dimethylformamide (5 ml) and toluene (50 ml), cooled at 0° C., oxalyl chloride (1.1 ml, 25.7 mmoles) is slowly added. After having maintained the reaction mixture under stirring for 12 hours at room temperature, it is evaporated under vacuum. To the obtained crude product, dissolved in tetrahydrofuran (40 ml) N-methyl diethanolamine (4.05 g, 38.55 mmoles) is added and the obtained solution is maintained under stirring at room temperature for 6 hours. The reaction mixture is evaporated at reduced pressure. The residue is treated with ethyl acetate and washed with water. The organic phase is anhydrified with sodium sulphate and dried. The crude product is purified by chromatography on silica gel, eluting with n-hexane/ethyl acetate 3/7 (ratio by volume). [2-[4-[(4-chlorophenyl)-phenylmethyl]1-piperazinyl]ethoxy]acetic acid [N-methyl-N-(2-hydroxyethyl)]-2-aminoethyl ester is obtained.

b) Preparation of [2-[4-[(4-chlorophenyl)phenylmethyl]1-piperazinyl]ethoxy]acetic acid [N-methyl-N-(2-chloroethyl)]-2-aminoethyl ester To a solution of [2-[4-[(4-chlorophenyl)phenylmethyl]1-piperazinyl]ethoxy]acetic acid [N-methyl-N-(2-hydroxyethyl)]-2-aminoethyl ester (3.8 g, 7.75 mmoles) in chloroform (70 ml), cooled at 0° C., thionyl chloride (0.58 ml, 8.06 mmoles) in chloroform (30 ml) is added. The solution is left at 0° C. for 30 minutes under stirring and then heated at 40° C. for 6 hours. The reaction is then washed with a saturated sodium bicarbonate solution and subsequently with water. The organic phase, anhydrified with sodium sulphate, is evaporated at reduced pressure. The crude product is purified by chromatography on silica gel, eluting with n-hexane/ethyl acetate 7/3 (ratio by volume). [2-[4-[(4-chlorophenyl)phenylmethyl]1-piperazinyl]ethoxy]acetic acid [N-methyl-N-(2-chloroethyl)]-2-aminoethyl ester is obtained.

c) Preparation of [2-[4-[(4-chlorophenyl)phenylmethyl]1-piperazinyl]ethoxy]acetic acid [N-methyl-N-(2-nitroxyethyl)]-2-aminoethyl ester To a solution of [2-[4-[(4-chlorophenyl)phenyl methyl]1-piperazinyl]ethoxy]acetic acid [N-methyl-N-(2-chloroethyl)]-2-aminoethyl ester (2.3 g, 4.52 mmoles) in acetonitrile (100 ml), silver nitrate (1.53 g, 9.04 mmoles) is added. The reaction mixture is heated to 80° C. away from light for 48 hours, then brought again to room temperature, filtered to remove the silver salts and evaporated at reduced pressure. The residue is purified by chromatography on silica gel, eluting with n-hexane/ethyl acetate 7/3 (ratio by volume). [2-[4-[(4-chlorophenyl)phenylmethyl]1-piperazinyl]ethoxy]acetic acid [N-methyl-N-(2-nitroxyethyl)]-2-aminoethyl ester is obtained.

Yield: 23%.

| Elementary analysis: | C | H | N | Cl |
|---|---|---|---|---|
| Calculated | 58.37% | 6.59% | 10.47% | 6.63% |
| Found | 58.38% | 6.58% | 10.45% | 6.60% |

EXAMPLE 6

Preparation of 6-[D(−)-α-aminophenyl acetamido]penicillinic acid 5-(nitroxy)ethyloxyethyl ester

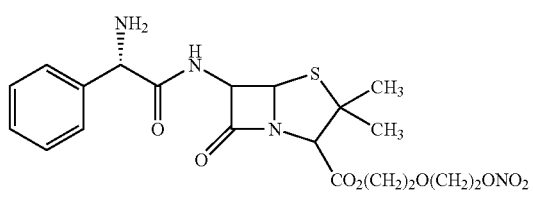
(E-6)

The precursor drug is ampicillin of formula

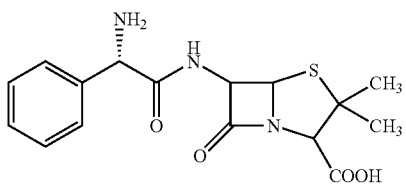
(E-6a)

The precursor compound of B is diethylenglycol.

a) Preparation of 6-[D(-)-α-tert-butoxycarbonylamino phenyl acetamido]penicillinic acid To a solution of ampicillin (3 g, 8.58 mmoles) in a dioxane (18 ml) and water (25 ml) mixture, triethylamine (2.1 ml, 15.3 mmoles) and di-tert-butyldicarbonate (2.24 g, 10.29 mmoles) are added. The reaction mixture is left under stirring at room temperature for 24 hours, then concentrated at reduced pressure. The residue is treated by subsequent additions of a 1% HCl solution until the pH of the aqueous phase is equal to 7. One extracts with ethyl acetate. The organic phase is anhydrified with sodium sulphate and then evaporated under vacuum. 6-[D(-)-α-tert butoxycarbonylamino phenyl acetamido]penicillanic acid is obtained, which is used in the subsequent synthesis step without further purging.

b) Preparation of 6-[D(-)-α-tert-butoxycarbonylamino phenyl acetamido]penicillanic acid 5-(hydroxy)ethyloxyethyl ester To a solution of 6-[D(-)-α-tert-butoxycarbonylamino phenyl acetamido]penicillanic acid (3.8 g, 8.58 mmoles) in a mixture of N,N-dimethylformamide (5 ml) and toluene (40 ml), cooled at 0° C., oxalyl chloride (0.74 ml, 17.16 mmoles) is slowly added. The solution is left under stirring for 12 hours at room temperature and then evaporated under vacuum. The obtained crude product is dissolved in tetrahydrofuran (70 ml) and additioned with ethylenglycol (2.45 ml, 25.7 mmoles). The obtained solution is maintained under stirring at room temperature for 5 hours and then evaporated at reduced pressure. The residue is treated with ethyl acetate and washed with water. The organic phase, anhydrified with sodium sulphate, is dried. The crude product is purified by chromatography on silica gel, eluting with n-hexane/ethyl acetate 2/8 (ratio by volume). 6-[D(-)-α-tert -butoxycarbonylamino phenyl acetamido]penicillanic acid 5-(hydroxy) ethyloxyethyl ester is obtained.

c) Preparation of 6-[D(-)-α-tert-butoxycarbonylamino phenyl acetamido]penicillanic acid 5-(chloro)ethyloxyethyl ester To a solution of 6-[D(-)-α-tert-butoxycarbonylamino phenyl acetamido]penicillanic acid 5-(hydroxy)ethyloxy ethyl ester (3 g, 5.58 mmoles) in chloroform (70 ml), cooled at 0° C., thionyl chloride (0.42 ml, 5.8 mmoles) in chloroform (30 ml) is added. The solution is maintained under stirring at 0° C. for 30 minutes and then heated at 40° C. for 4 hours. Subsequently the mixture is washed with a saturated sodium bicarbonate solution and then with water. The organic phase is anhydrified with sodium sulphate and then evaporated at reduced pressure. The crude product is purified by chromatography on silica gel, eluting with n-hexane/ethyl acetate 1/1 (ratio by volume). 6-[D(-)-α-tert-butoxycarbonylamino phenyl acetamido]penicillanic acid 5-(chloro)ethyloxyethyl ester is obtained.

d) Preparation of 6-[D(-)-α-tert-butoxycarbonylamino phenyl acetamido]penicillanic acid 5-(nitroxy)ethyloxyethyl ester To a solution of 6-[D(-)-α-tert-butoxycarbonylamino phenyl acetamido]penicillanic acid 5 -(chloro) ethyloxyethyl ester (2.1 g, 3.77 mmoles) in acetonitrile (100 ml), silver nitrate (1.28 g, 7.54 mmoles) is added. The reaction mixture is heated at 80° C. for 24 hours away from light. It is cooled at room temperature, filtered to remove the silver salts and evaporated at reduced pressure. The residue is purified by chromatography on silica gel, eluting with n-hexane/ethyl acetate 1/1 (ratio by volume). 6-[D(-)-α-tert-butoxycarbonylamino phenyl acetamido]penicillanic acid 5-(nitroxy)ethyloxyethyl ester is obtained.

e) Preparation of 6-[D(-)-α-aminophenyl acetamido]penicillanic acid 5-(nitroxy)ethyloxyethyl ester To a solution of 6-[D(-)-α-tert-butoxycarbonylamino phenyl acetamido]penicillanic acid 5-(nitroxy)ethyloxy ethyl ester (1.5 g, 2.57 mmoles) in ethyl acetate (100 ml), cooled at 0° C., a 5N HCl solution in ethyl acetate (2.67 ml) is added. The solution is maintained at 0° C. under stirring for 7 hours and then filtered. The obtained solid is suspended in ethyl acetate and washed with a 5% w/v sodium carbonate solution. The organic phase is washed with water, anhydrified with sodium sulphate and evaporated at reduced pressure. The residue is purified by chromatography on silica gel eluting with n-hexane/ethyl acetate 1/1 (ratio by volume). 6-[D(-)-α-amino phenyl acetalmido]penicillanic acid 5-(nitroxy) ethyl oxyethyl ester is obtained. Yield: 13%.

| Elementary analysis: | C | H | N | S |
|---|---|---|---|---|
| Calculated | 49.79% | 5.43% | 11.61% | 6.64% |
| Found | 49.77% | 5.45% | 11.60% | 6.65% |

EXAMPLE 7

Preparation of 2-amino-1,9-dihydro-9-[[2-(4-nitroxybutyroyloxy)ethoxy)methyl]-6H-purin-6-one

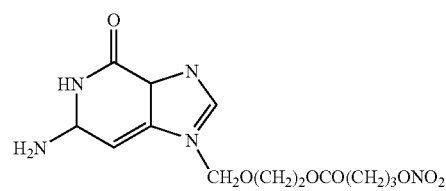
(E-7)

The precursor drug is aciclovir of formula

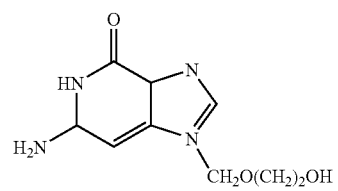
(E-7a)

The precursor compound of A is the 4-hydroxybutyric acid.
The compound (E-6) is synthetized according to the procedure described in Example 3. Yield: 14%.

| Elementary analysis: | C | H | N |
|---|---|---|---|
| Calculated | 42.36% | 4.74% | 24.70% |
| Found | 42.38% | 4.77% | 24.68%. |

EXAMPLE 8

Preparation of (8S-cis)-10-[(3-amino-2,3,6-trideoxy-α-L-lixo-hexopyranosyl)oxy]-7,8,9,10-tetrahydro-6,8,11-trihydroxy-8-[(4-nitroxybutyroyloxy)acetyl]-1-methoxy-5,12-naphthacendione

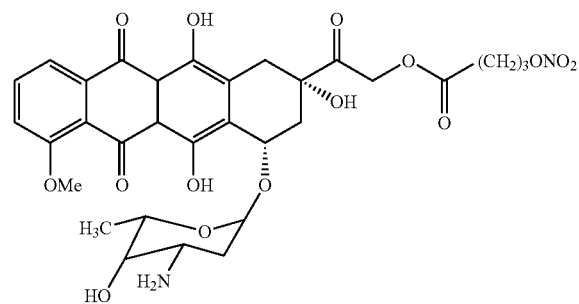

(E-8)

The precursor drug is doxorubicin of formula (E-8a)

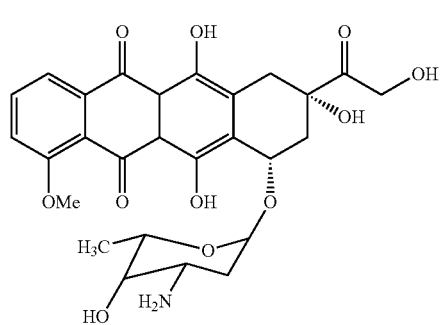

(E-8a)

The precursor compound of B is the 4-hydroxybutyric acid.
The compound is synthetized according to the procedure described in Example 1. Yield: 7%.

| Elementary analysis: | C | H | N |
|---|---|---|---|
| Calculated | 56.53% | 5.20% | 4.25% |
| Found | 56.55% | 5.22% | 4.23%. |

EXAMPLE 9

Preparation of di[1S-[1α,3α,7β,8β(2S*,4S*),8αβ]]2-2-dimethyl butyric acid 1,2,3,7,8,8α-hexahydro-3,7-dimethyl-8-[2-[tetrahydro-4-(6-nitroxyhexanoyloxy)-6-oxo-2H-pyran-2-yl]ethyl]-1-naphthalenyl ester

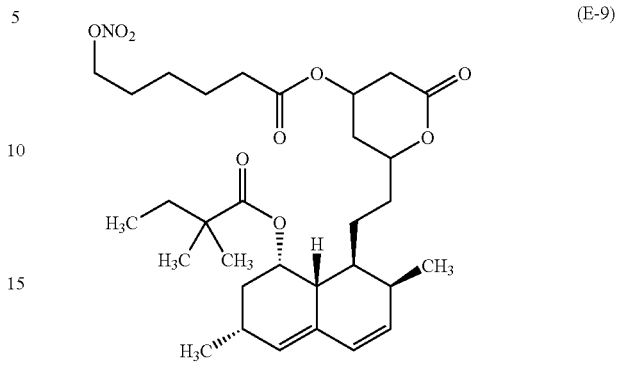

(E-9)

The precursor drug is simvastatine of formula

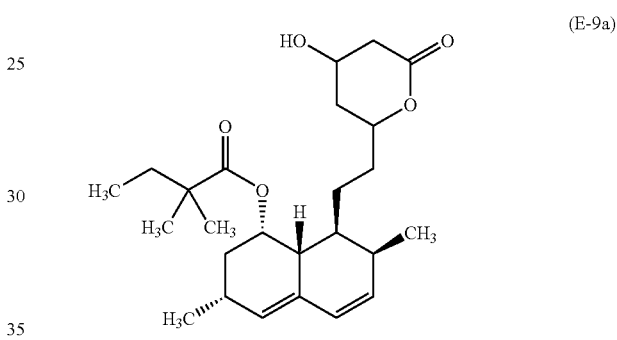

(E-9a)

The precursor of the bridging bond B is 6-hydroxyhexanoic acid.

a) Preparation of [1S-[1α,3α,7β,8β(2S*,4S*),8αβ]]2-2-dimethyl butyric acid 1,2,3,7,8,8α-hexahydro-3,7-dimethyl-8-[2-[tetrahydro-4-(6-bromohexanoyloxy)-6-oxo-2H-pyran-2-yl]ethyl]-1-naphthalenyl ester To a solution of simvastatine (4 g, 9.56 mmoles) in chloroform (50 ml)-and N,N-dimethylformamide (20 ml), 6-bromo caproic acid (1.86 g, 9.56 mmoles), N,N'-dicyclohexylcarbodiimide (1.97 g, 9.56 mmoles) and 4-dimethyl amino pyridine (52 mg, 0.43 mmoles) are added. The reaction mixture is maintained under stirring at room temperature for 24 hours, then diluted with chloroform and washed with water. The organic phase, anhydrified with sodium sulphate, is evaporated at reduced pressure. The crude product is purified by chromatography on silica gel, eluting with n-hexane/ethyl acetate 1/1 (ratio by volume). [1S-[1α,3α,7β,8β(2S*,4S*),8αβ]]2-2-dimethyl butyric acid 1,2,3,7,8,8α-hexahydro-3,7-dimethyl-8-[2-[tetrahydro-4-(6-bromohexanoyloxy)-6-oxo-2H-pyran-2-yl]ethyl]-1-naphthalenyl ester is obtained.

b) Preparation of [1S-[1α,3α,7β,8β(2S*,4S*),8αβ]]2-2-dimethyl butyric acid 1,2,3,7,8,8α-hexahydro-3,7-dimethyl-8-[2-[tetrahydro-4-(6-nitroxyhexanoyloxy)-6-oxo-2H-pyran-2-yl]ethyl]-1-naphthalenyl ester To a solution of [1S-[1α,3α,7β,8β(2S*,4S*),8αβ]]2-2-dimethyl butyric acid 1,2,3,7,8,8α-hexahydro-3,7-dimethyl-8-[2-[tetrahydro-4-(6-bromohexanoyloxy)-6-oxo-2H-pyran-2-yl]ethyl]-1-naphthalenyl ester (1 g, 1.67 mmoles) in acetonitrile (60 ml) silver nitrate (0.57 g, 3.35 mmoles) is added. The reaction mixture is heated for 6 hours at 80° C. away from light, then it is cooled to room temperature, filtered to remove the silver salts and the organic phase is evaporated under reduced pressure. The residue is purified by chromatography on silica gel, eluting with n-hexane/ethyl acetate 1/1 (ratio by volume). [1S -[1α,3α,7β,8β(2S*,4S*),8αβ]]2-2-dimethyl butyric acid 1,2,3,7,8,8α-hexahydro-3,7-dimethyl-8-[2-[tetrahydro-4-(6-nitroxyhexanoyloxy)-6-oxo-2H-pyran-2-yl]ethyl]-1-naphthalenyl ester is obtained. Yield: 13%.

| Elementary analysis: | C | H | N |
|---|---|---|---|
| Calculated | 62.71% | 7.97% | 2.35% |
| Found | 62.74% | 7.99% | 2.33% |

EXAMPLE 10

Preparation of 6-(nitroxy)hexanoic acid theophylline ester

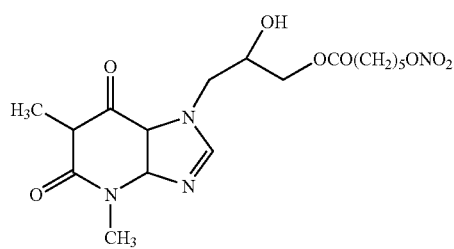
(E-10)

The precursor drug is diphylline of formula:

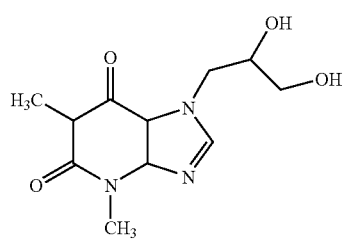
(E-10a)

The precursor compound of B is the 6-hydroxyhexanoic acid.
The compound of formula (E-10) is synthetized according to the procedure described in Example 9. Yield: 23%.

| Elementary analysis: | C | H | N |
|---|---|---|---|
| Calculated | 44.76% | 5.39% | 16.31% |
| Found | 44.77% | 5.41% | 16.33%. |

EXAMPLE 11

Preparation of 9-[4-nitroxy)butyroylamino]-1,2,3,4-tetrahydroacridine

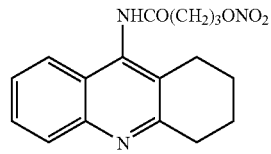
(E-11)

The precursor drug is tacrine of formula

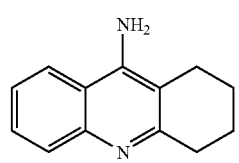
(E-11a)

The precursor compound of B is the 4-hydroxybutyric acid.

a) Preparation of 9-[4-bromo)butyroylamino]-1,2,3,4-tetrahydroacridine

To a solution of tacrine (4 g, 20.17 mmoles) in chloroform (50 ml) and N,N-dimethylformamide (15 ml), 4-bromobutyroylchloride (3.5 ml, 30.25 mmoles) is added. The reaction mixture is maintained under stirring at room temperature for 6 hours and then diluted with chloroform and washed with water. The organic phase, anhydrified with sodium sulphate, is evaporated at reduced pressure. The crude product is purged by chromatography on silica gel, eluting with n-hexane/ethyl acetate 8/2 (ratio by volume). 9-[4-bromo)butyroylamino]-1,2,3,4-tetrahydroacridine is obtained.

b) Preparation of 9-[4-nitroxy)butyroylamino]-1,2,3,4-tetrahydroacridine

To a solution of 9-[4-bromo)butyroylamino]-1,2,3,4-tetrahydroacridine (3.5 g, 10.56 mmoles) in acetonitrile (150 ml) silver nitrate (2.08 g, 12.68 mmoles) is added. The reaction mixture is heated at 80° C. under stirring for 6 hours away from light. It is cooled to room temperature, filtered to remove the silver salts and evaporated under reduced pressure. The residue is purified by chromatography on silica gel, eluting with n-hexane/ethyl acetate 8/2 (ratio by volume). 9-[4-nitroxy)butyroylamino]-1,2,3,4-tetrahydroacridine is obtained. Yield: 33%.

| Elementary analysis: | C | H | N |
|---|---|---|---|
| Calculated | 62.00% | 5.81% | 12.76% |
| Found | 62.02% | 5.83% | 12.77% |

EXAMPLE 12

Preparation of (S)-α-(2-chlorophenyl)-6,7-dihydrothieno[3,2-c-]-pyridin-5(4H)acetic acid 5-(nitroxy)ethylthioethyl ester

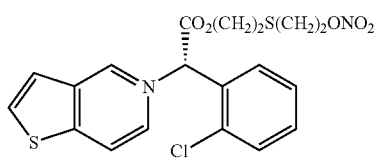

(E-12)

The precursor drug is clopidrogel of formula:

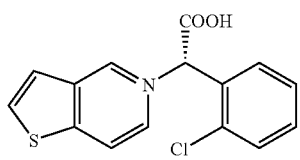

(E-12a)

The precursor compound of A is the thiodiethylenglycol of formula HO—(CH$_2$)$_2$—S—(CH$_2$)$_2$—OH.

The compound of formula (E-12) is synthetized according to the procedure described in Example 5, using thiodiethylenglycol in substitution of diethylenglycol. Yield: 56%.

| Elementary analysis: | C | H | N | Cl | S |
|---|---|---|---|---|---|
| Calculated | 49.94% | 4.63% | 6.13% | 7.76% | 14.03% |
| Found | 49.93% | 4.63% | 6.10% | 7.75% | 14.01% |

EXAMPLE 13

Preparation of 5-methoxy-2-[[4-(4-nitroxybutyroyloxy)-3,5-dimethyl-2-pyridinyl)methyl]sulphinyl]-1H-benzoimidazol (E-13)

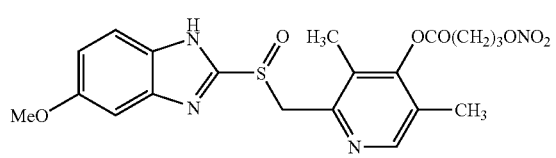

The precursor drug is demethylomeprazol of formula:

(E-13a)

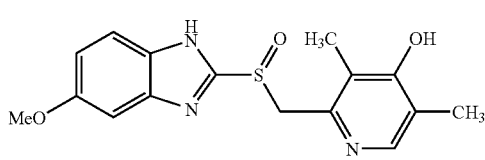

The precursor compound of B is 4-hydroxybutyric acid.

The compound of formula (E-13) is synthetized according to the procedure described in Example 1. Yield: 22%.

| Elementary analysis: | C | H | N | S |
|---|---|---|---|---|
| Calculated | 51.94% | 4.79% | 12.12% | 6.93 |
| Found | 51.93% | 4.77% | 12.11% | 6.94% |

EXAMPLE 14

Preparation of 2-[(2,6-dichlorophenyl)amino]benzene acetic acid [N-methyl-N-(2-hydroxyethyl)]-2-aminoethyl ester (E-14)

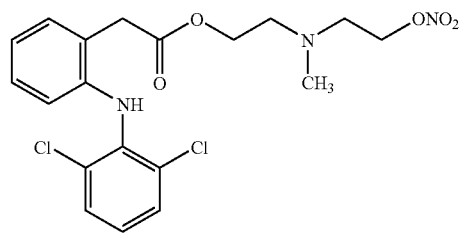

The precursor drug is diclofenac of formula:

(E-14a)

The precursor compound of B is N-methyldiethanolamine of formula HO—(CH$_2$)$_2$—N(CH$_3$)—(CH$_2$)$_2$—OH.

The compound is synthetized according to the procedure described in Example 5. Yield: 52%.

| Elementary analysis: | C | H | N | Cl |
|---|---|---|---|---|
| Calculated | 51.60% | 4.78% | 9.50% | 16.03% |
| Found | 51.60% | 4.77% | 9.53% | 16.04% |

EXAMPLE 15

Preparation of 3-(4-hydroxy-3-methoxyphenyl)-2-propenoic acid 4-(nitroxy)butylester

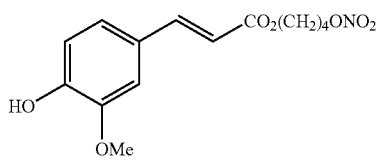

(E-15)

The precursor drug is ferulic acid of formula (E-15a)

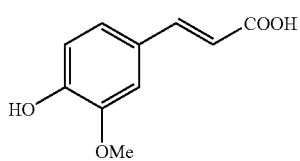

(E-15a)

The precursor compound of B is 1,4-butandiol.

a) Preparation of 3-(4-hydroxy-3-methoxyphenyl)-2-propenoic acid 4-bromo butyl ester To a solution of ferulic acid (10 g, 51.51 mmoles) in tetrahydrofuran (400 ml), triphenylphosphine (27 g, 103 mmoles) and carbon tetrabromide (34.1 g, 103 mmoles) are added. The reaction mixture is maintained under stirring at room temperature for 4 hours, then filtered and evaporated under reduced pressure. The reaction crude product is purified by chromatography on silica gel, eluting with n-hexane/ethyl acetate 7/3 (ratio by volume). 3-(4-hydroxy-3-methoxyphenyl)-2-propenoic acid 4-bromo butyl ester is obtained.

b) Preparation of 3-(4-hydroxy-3-methoxyphenyl)-2-propenoic acid 4-(nitroxy)butyl ester To a solution of 3-(4-hydroxy-3-methoxyphenyl)-2-propenoic acid 4-bromobutyl ester (2.72 g, 6.89 mmoles) in acetonitrile (25 ml) silver nitrate (1.48 g, 8.71 mmoles) is added. The reaction mixture is maintained under stirring and heated at 80° C. for 7 hours away from light, then cooled at room temperature, filtered to remove the silver salts and evaporated under reduced pressure. The residue is purified by chromatography on silica gel, eluting with n-hexane/ethyl acetate 7/3 (ratio by volume). 3-(4-hydroxy-3-methoxyphenyl)-2-propenoic acid 4-(nitroxy)butyl ester is obtained. Yield: 56%.

| Elementary analysis: | C | H | N |
|---|---|---|---|
| Calculated | 54.02% | 5.50% | 4.50% |
| Found | 54.00% | 5.52% | 4.49% |

PHARMACOLOGICAL TESTS

EXAMPLE

Acute Toxicity

Acute toxicity has been evaluated by administering to a group of 10 rats weighing 20 g a single dose of each of the compounds to be tested, by cannula, by os in an aqueous 2% w/v suspension of carboxymethylcellulose.

The animals are kept under observation for 14 days. In no animal of the group toxic symptoms appeared even after a 100 mg/Kg dose administration.

Example F1

Test 1—experimental model in vivo with N-ethylmaleimide (NEM): study of the gastric tolerability of some drugs screened as precursors of the compounds of the invention.

The animals (rats, weight about 200 g) are distributed in the following groups (No. 10 animals for group):

A) Control Groups:
1° group: treatment: only carrier (aqueous suspension 1% w/v of carboxymethylcellulose, dose: 5 ml/Kg when the drug is administered by os, physiologic solution when by parenteral route),
2° group: treatment: carrier+NEM, B) Groups Administered with Each Drug:
group I: treatment: carrier+drug,
group II: treatment: carrier+drug+NEM.

The drugs assayed in this experiment are the following (Table I): indomethacin, ambroxol, mesalamine, sodic alendronate, tacrine, omeprazol, misoprostol.

Indomethacin, ambroxol and alendronate are administered by os, mesalamine by intracolonic (rectal) route and tacrine, omeprazol, misoprostol by subcutaneous route.

The maximum tolerated dose, determined by administering each substance by the above said routes to the animals not treated with NEM, is reported in Table I. With higher doses than those reported in the Table, enteropathy, diarrhoea, depression, tremor and sedation have appeared in the animals.

In this experimental model the animals are at first treated with NEM by subcutaneous injection at a dose of 25 mg/kg in physiologic solution. The drug is administered one hour later, in suspension in the carrier. Animals are sacrificed after 24 hours and evaluation of the damage to the gastrointestinal mucosa is made by counting the number of rats, inside each group, with lesions to the stomach at a visual inspection. The total number of said rats is then divided by the total number of rats of the group and multiplied by 100. The thus obtained percentages are reported in Table I. The Table shows that in the groups of rats treated with said drugs without NEM, no gastric lesions were detectable.

All the rats of group II (treated with NEM) showed gastric lesions after administration with the following drugs: indomethacin, ambroxol, mesalamine, sodic alendronate, tacrine. Said drugs therefore can be used in the synthesis of the products of the invention.

Omeprazol and misoprostol cannot instead be used, on the basis of the results provided in test 1, for preparing the products of the invention.

Example F2

Test 2 (in vitro): inhibition of apoptosis (DNA fragmentation) induced in the endothelial cells by CIP in the presence of some drugs screened as precursors of the compounds of the invention.

The following precursor drugs (Table II): indomethacin, paracetamol, clopidogrel, salbutamol, ambroxol, sodic alendronate, diphylline, cetirizine, enalapril, nicotinamide, ampicilline, aciclovir, mesalamine, tacrine, simvastine, omeprazol have been tested.

Human endothelial cells of the umbilical vein are prepared according to a standard method. Fresh umbilical veins are filled with a collagenase solution 0.1% by weight and incubated at 37° C. for 5 minutes.

Subsequently the veins are perfused with the medium M 199 (GIBCO, Grand Island, N.Y.) pH 7.4 with 0.1% (weight/ volume) of collagenase, added with 10% of bovine fetus serum (10 mcg/ml), sodium heparin (50 mcg/ml), thimidine (2.4 mcg/ml), glutamine (230 mcg/ml), penicillin (100 UI/ml), streptomycin (100 mcg/ml) and streptomycin B (0.125 mcg/ml). The cells are collected from the perfusate by centrifugation at 800 rpm and harvested in culture flasks T-75, pretreated with human fibronectin. Cells are then harvested in the same medium, added with bovine hypothalamic growth factor (100 ng/ml). When the cells of the primary cell culture (the cells directly removed from ex-vivo umbilical vein) form a single layer of confluent cells (about 8,000,000 cells/flask), harvesting is stopped and the layers are washed and trypsinized. The cellular suspensions are transferred into wells of a culture plate having 24 wells, half of said wells being added with the same culture medium containing the drug at a $10^{-4}$M concentration, and harvested in a thermostat at 37° C. at a constant moisture (90%), $CO_2$=5%. When the drug is not soluble in the culture medium, it is formerly dissolved in a small amount of dimethylsulphoxide. The maximum amount of dimethylsulphoxide which can be added to the culture medium is 0.5%. Only the cells coming from these first subcultures are used for the tests with cumene hydroperoxide (CIP). The cells are identified as endothelial cells by morphological examination and by the specific immunological reaction towards factor VIII; these cultures did never show contaminations from myocytes or fibroblasts.

Before starting the test, the cellular culture medium is removed and the cellular layers are carefully washed with a standard physiologic solution buffered with phosphate 0.1 M pH 7.0, at the temperature of 37° C. The content of each well is then incubated for one hour with a CIP suspension in the culture medium at a 5 mM concentration. Evaluation of the cellular damage (apoptosis) is carried out by determining the percent variation of the DNA fragmentation in the cultures containing the drug+CIP with respect to the controls treated with CIP only. Said % variation of DNA fragmentation is determined by evaluating the fluorescence variation by a BX60 Olympus microscope (Olympus Co., Roma) set at the wave length of 405-450 nm, of the test samples with respect to the optical density of the controls. The fluorescence of each sample was determined on 5 replicates. Statistic evaluation has been made with t Student test ($p<0.01$).

Results are given in Table II and show that indomethacin, paracetamol, clopidogrel, salbutamol, sodic alendronate, diphylline, cetirizine, enalapril, nicotinamide, ampicilline, aciclovir, tacrine, omeprazol do not significantly inhibit apoptosis; these drugs can therefore be used for preparing the products of the invention.

On the contrary ambroxol, mesalamine and simvastatine inhibit apoptosis. Therefore on the basis of the results of test 2 these compounds could not be used for preparing the products of the invention.

Example F3

Test 3—experimental in vivo model with $N^w$-nitro-L-arginine-methyl ester (L-NAME): gastric tolerability (gastrointestinal damage incidence), hepatic (GPT dosage, glutamic-pyruvic transaminase) and cardiovascular (blood pressure) of some drugs screened as precursors of the compounds of the invention.

The experimental model adopted is according to J. Clin. Investigation 90, 278-281, 1992.

The endothelial dysfunction is evaluated by determining the damage induced by L-NAME administration to the gastrointestinal mucosa, the hepatic damage (GPT increase), and the vascular endothelium or cardiovascular damage as blood hypertension.

The animals (rats, average weight 200 g) are divided in groups as herein below described. The group receiving L-NAME is treated for 4 weeks with said compound dissolved at the concentration of 400 mg/litre in drinking water. The following groups (No. 10 animals for group) are constituted:

A) Control Groups:

1° group: treatment: only carrier (aqueous suspension 1% w/v of carboxymethylcellulose, dose: 5 ml/Kg when the drug is administered by os, physiologic solution when by parenteral route), 2° group: treatment: carrier+L-NAME, B) Groups Treated with the Drug:

3° group: treatment: carrier+drug,

4° group: treatment: carrier+drug+L-NAME.

The drugs used in the test are paracetamol, doxorubicine, simvastatine, omeprazol and misoprostol. Each drug is administered once a day for 4 weeks.

The maximum tolerated dose of the drug being administered to the animals is determined by evaluating, in a separate dose scaling up experiment on untreated animals, the appearance in the animals of symptoms such as enteropathy, diarrhoea, depression, tremor, sedation.

At the end of the four weeks access to water is prevented and after 24 hours the animals are sacrificed.

One hour before the sacrifice blood pressure is determined and a blood pressure increase is taken as an indication of a damage being occurred to vascular endothelium.

The damage to the gastric mucosa is evaluated as previously mentioned in test 1 (ex. F1). The hepatic damage is determined by evaluation after the sacrifice of the glutamic-pyruvic pyruvic transaminase (GPT increase).

The drug meets test 3 and it can therefore be used for preparing the compounds of the invention, when in the group of rats treated with L-NAME+drug+carrier, an higher hepatic damage (higher GPT values) and/or higher gastric damage and/or higher cardiovascular damage (higher blood pessure) are found in comparison with the group treated with the carrier only, or the group treated with carrier+drug, or the group treated with carrier+L-NAME.

The test results are reported in Table IV. The % gastric lesions have been determined as in Test 1. The % GPT and % blood pressure values are referred to the corresponding value found in the animals of the 1st group of the control groups. The average value of the blood pressure in this group was of 105±8 mmHg.

The results obtained show that paracetamol, doxorubicine and simvastatine cause hepatic damage and gastroenteropathy (GPT values and the gastric lesions are % higher compared both with the corresponding groups treated with the drug, in the absence of L-NAME, and with the controls treated with L-NAME).

These drugs can therefore be used for preparing the products of the invention.

Omeprazol and misoprostol should not instead be used, on the basis of this test, for preparing the products of the invention.

Example F4

Test 4A: Activity of some substances used as precursors of B in the products according to the invention in inhibiting the haemolysis of erythrocytes induced by cumene peroxide.

Test 4a is performed according to the method described by R. Maffei Facino, M. Carini G. Aldini, M. T. Calloni, Drugs Exptl. Clin. Res. XXIII (5/8) 157-165 1997.

Erythrocytes isolated by using standard procedures from Wistar male rats (Charles River), are suspended in a physiological solution buffered at pH 7.4 with phosphate buffer and equilibrated at 4° C. for 4 days. then an aliquot of said suspension is centrifuged at 1000 rpm for 5 minutes and 0.1 ml of the centrifuged erythrocytes are diluted to 50 ml with sodium phosphate buffer of the same above molarity, thus obtaining a suspension containing 0.2% by volume of erythrocytes. 3.5 ml portions of said diluted suspension are added of 0.1 ml of an alcoholic solution of cumene hydroperoxide 9.72 mM, which causes lysis of the cells. The resulting suspension is then incubated at 37° C. An increase of the turbidity is observed in the suspension. The process of cell lysis is followed by turbidimetry at 710 nm, by determining the optical density (or the transmittance) at intervals of 30 minutes. The time at which there is the maximum amount of cell lysed, that corresponds to the maximum turbidity of the suspension, is taken as the Tmax and it is assumed to correspond to a cell lysis of 100%. 0.2 ml of 38 mM ethanol solutions of the test compounds to be used as precursors of B are added to aliquots of 3.5 ml of the diluted suspension of erythrocytes above prepared, the resulting suspension preincubated for 30 minutes, 0.1 ml of an alcoholic solution of cumene hydroperoxide 10.26 mM is then added, and at the time Tmax it is determined the percentage of haemolysis inhibition in the sample from the ratio, multiplied by 100, between the absorbance of the suspension of the sample containing the erythrocytes, the precursor of B and cumene hydroperoxide respectively and that of the suspension containing the erythrocytes and cumene hydroperoxide; the precursors of B meet the test if they inhibit the haemolysis induced by cumene hydroperoxide by a percentage >15%;

In Table V are reported the results obtained with the following substances: N-methyldiethanolamine, diethylenglycol, thio-diethylenglycol, 1,4-butandiol, butanol and diethanolamine.

Table v shows that:
N-methyldiethanolamine, diethylenglycol, thiodiethylen glycol, 1,4-butandiol meet test 4 since they inhibit the haemolysis induced by cumene peroxide to an extent higher than 15%.
Butanol and diethanolamine are instead ineffective, since they inhibit the haemolysis induced by cumene hydroperoxide to an extent lower than 15% and therefore they cannot be used as precursors of B in the synthesis of the compounds according to the present invention.

Example F5

Test 5: Activity of compounds used as precursors of B in Inhibiting radical production from $FE^{II}$ compounds.

0.1 ml aliquots of $10^{-4}$ M methanolic solutions in methanol of, respectively, 1-4 butandiol, of N-methyl-diethanolamine of di-ethylenglycol and of thiodiethylenglycol, are added to test tubes containing an aqueous solution obtained by mixing 0.2 ml of 2 mM deoxyribose, 0.4 ml of buffer phosphate pH 7.4 100 mM and 0.1 ml of 1 mM $Fe^{II}(NH_4)_2(SO_4)_2$ in 2 mM HCl. The test tubes are then kept at a temperature of 37° C. for one hour. Then in each test tube are added in the order 0.5 ml of a 2.8% solution in trichloroacetic acid in water and 0.5 ml of an aqueous solution 0.1 M thio barbituric acid. A reference blank is constituted by substituting the above 0.1 ml aliquots of the test compound methanolic solutions with 0.1 ml of methanol. The test tubes are closed and heated in an oil bath at 100° C. for 15 minutes. A pink coloration develops the intensity of which is proportional to the quantity of deoxyribose undergone to radical oxidative degradation. The solutions are cooled at room temperature and their absorbances at 532 nm are read against the blank.

The inhibition induced by the precursor of B in the confront of radical production from $Fe^{II}$ is determined as a percentage by means of the following formula:

$$(1-A_s/A_c) \times 100$$

wherein $A_s$ and $A_c$ are respectively the absorbance values of the solution containing the tested compound+the iron salt and that of the solution containing only the iron salt.

The results are reported in the attached Table III, in which it is shown that the compounds under test are ineffective in inhibiting the radical production from the iron ion.

Therefore these compounds can be used as precursor compounds of B for obtaining the compounds of the present invention.

Example F6

It has been evaluated the activity of some of the compounds object of the present invention and of the corresponding precursor drugs in inhibiting DNA degradation (apoptosis) in endothelial cells exposed to the action of hydrogen peroxide (HP).

Hydrogen peroxide is a mild oxidant and is considered as an essential mediating agent in pathologies associated with oxidative stress (B. Halliwell, J. Gutteridge "Free Radicals in Biology and Medicine", page 416, 1993). Therefore the pharmacological activity of compounds to be used under oxidative stress conditions is evaluated through their capability of neutralizing the cytolesive effects of the hydrogen peroxide (B. Halliwell, J. Gutteridge "Free Radicals in Biology and Medicine", page 416, 1993).

The method described by Herman et Al. (Herman C., Zeiner M. A., Dimmeler S., Arterioscler. Thromb. vasc. Biol. 17 (12), 3588-82, 1997).

Human endothelial cells of the umbilical vein are prepared according to a standard method. Fresh umbilical veins, just removed, are filled with a solution of collagenase at 0.1% and incubated at 37° C. for 5 minutes.

Subsequently the veins are perfused with medium M 199 (GIBCO, Grand Island, N.Y.) pH 7.4 containing 20% of human serum. The cells are collected from the perfusate by centrifugation at 800 rpm and harvested in culture flasks T-75, pretreated with human fibronectin. Cells are then harvested in the medium pH 7.4, containing 20% human serum, low molecular weight sodium heparin (30 mcg/ml), penicillin (100,000 UI/ml) and bovine hypothalamic growth factor (100 ng/ml). The primary confluent monolayers (about 8,000,000 cells/flask) are washed and trypsinized. The cellular suspensions are transferred into each well of a culture plate with 24 hollows and harvested in a thermostat at 37° C. at constant humidity (90%), $CO_2=5\%$. Only the cells coming from these first subcultures are used for the experiments with HP. The cells are identified as endothelial cells by morphological examination and by specific dye-reactions. The cultures never showed contaminations from myocytes or fibroblasts.

In order to perform the experiment with HP, the cellular culture medium is removed and the cellular layers are carefully washed with a physiological solution buffered with 0.1 M phosphate pH 7.0 at the temperature of 37° C. The cells are then incubated for 18 hours with HP at the concentration of 200 μmoles/l.

The evaluation of the cellular damage (apoptosis) is carried out by determining the percent variation of the DNA fragmentation in the sample with respect to the control added only of HP. The products under assay are tested at the concentration of 100 μmoles/l. If said products are found insoluble in the culture medium, they are dissolved in a small amount of dimethylsulphoxide (DMSO), taking into account that the maximum DMSO amount which can be added to the culture medium is 0.5% v/v. 3 replicates of each sample are made.

The results are reported in Table VI and show that in those samples of cell culture treated with the compounds of the invention, the inhibition of the DNA fragmentation, or in more general terms of cellular damage, is at least twice than that occurring in the samples treated with the corresponding precursors.

Example F7

Gastric lesions induced by administration of the compounds of the invention in the confront of the corresponding drug precursor.

Groups of male Wistar rats weighing 180-200 g (No. 10 rats for group), fasted from 17 hours, have been fed by os, by a cannula, with a 2% carboxymethylcellulose suspension in water (carrier) added with one of the following compounds:

Diclofenac, dose of 20 mg/kg p.o.,
Diclofenac nitroxyester according to Ex. 14, at the same above dose p.o.,
Ambroxol, 100 mg/kg p.o.,
Ambroxol nitroxyester according to Example 3 at the same above dose p.o.,
Alendronate, dose 100 mg/kg p.o.,
Nitroxyester of the alendronic acid according to Ex. 4 at the same above dose, p.o.

Tacrine and the corresponding nitroxyester obtained according to Ex. 11, have been administered to the rats by subcutaneous route in a physiological solution at the dose of 10 mg/kg.

The animals have been sacrificed 6 hours after the administration. The gastrointestinal mucosa has been removed and inspected. The incidence of the gastrointestinal damage has been evaluated as described in experiment F1.

The results are reported in Table VII and show that the compounds of the invention do not either induce gastric lesions or, in the case, the incidence of said lesions is much lower than that found with the precursor drug.

EXAMPLE 16

Synthesis of (S)-1-[N-[1-(ethoxycarbonyl)-3-phenylpropyl]-L-alanyl]-L-proline[2-(N-methyl,N'-(2-nitroxy)ethyl)-ammino]ethyl ester of formula

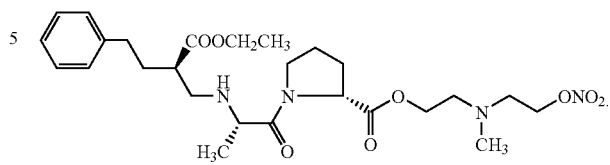

The precursor is enalapril having formula:

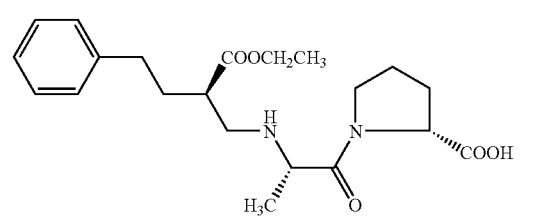

and the precursor of B is N-metil-diethanolamine of formula:

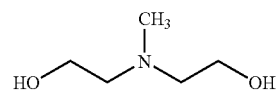

The compound of formula (E-16) is synthetized according to the process described in Example 5. Yield: 19%
Elemental analysis:

| Calculated % | C 58.19 | H 7.51 | N 10.44 |
|---|---|---|---|
| Found % | C 58.22 | H 7.53 | N 10.42 |

EXAMPLE 17

Synthesis of (4-nitroxy)-butanoic acid 1-[(1-methylethyl) amino]-3-(1-naphthalen oxy)-2-propyl ester of formula

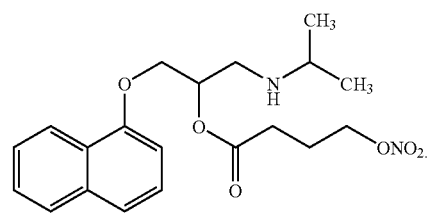

The precursor is propranolol having the following formula:

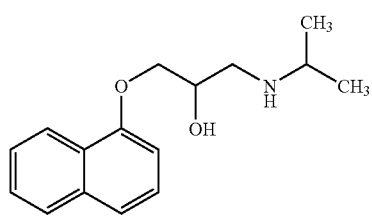
(E-17a)

and the precursor of B is 4-hydroxy-butanoic acid. Compound (E-17) is synthetized according to Example 1.
Yield: 25%.
Elemental analysis:

| Calculated % | C 61.53 | H 6.71 | N 7.17 |
|---|---|---|---|
| Found % | C 61.58 | H 6.74 | N 7.15 |

EXAMPLE 18

Synthesis of butandioic acid [1-[5-(2,5-dihydro-5-oxo-3-furanyl)-3-methyl-2-benzofuranyl]ethyl [(2-nitroxy)ethoxy]ethyl diester of formula Compound (E-18) is synthetized according to Example 6.
Yield: 16%.
Elemental analysis:

| Calculated % | C 56.21 | H 5.13 | N 2.85 |
|---|---|---|---|
| Found % | C 56.26 | H 5.10 | N 2.90 |

EXAMPLE 19

N-[[6-methoxy-5-(trifluoromethyl)-1-naphtalenyl[thioxomethyl]-N-methylglycine [2-(N-methyl,N'-(2-nitroxy)ethyl)ammino]ethyl ester of formula

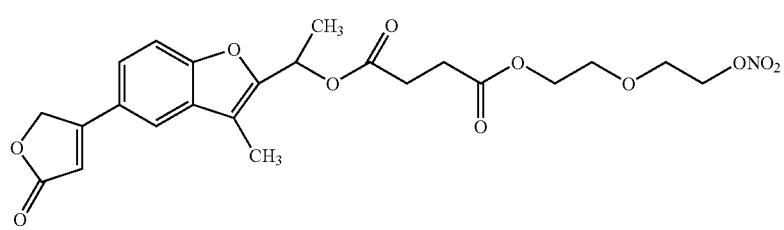
(E-19)

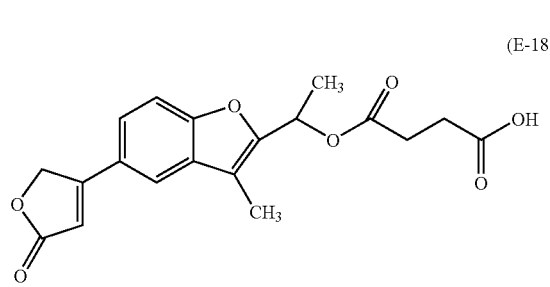
(E-18)

The precursor drug is Benfurodil hemisuccinate having formula:

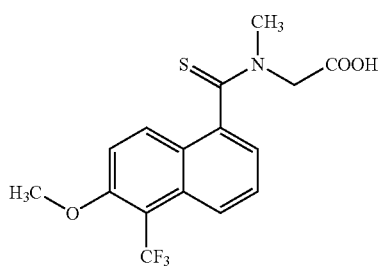

The precursor drug is tolrestat of formula:

(E-19a)

and the compound precursor of B is diethylene glycol of formula:

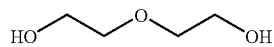

and the precursor of B is N-metil diethanolamine of formula:

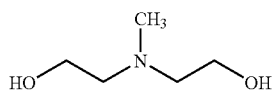

Compound (E-19) was synthetized according to Example 5.
Yield: 12%
Elemental analysis:

| Calc. % | C 50.10 | H 4.80 | N: 8.35 | S 6.30 | F 11.32 |
|---|---|---|---|---|---|
| Found % | C 50.15 | H 4.82 | N 8.30 | S 6.25 | F 11.34 |

EXAMPLE 20

Synthesis of (8S-cis)-10[(3-amino,2,3,6-tri-deoxy-α-L-lyxo-exopyranosyl)oxy]-7,8,9,10-tetrahydro,6,8,11-trihydroxy-8-[[3-methoxy-4-(4-nitroxy butanoyl-oxy]methyl-oxo]-1-methoxy-5,12-naphtacenedione of formula

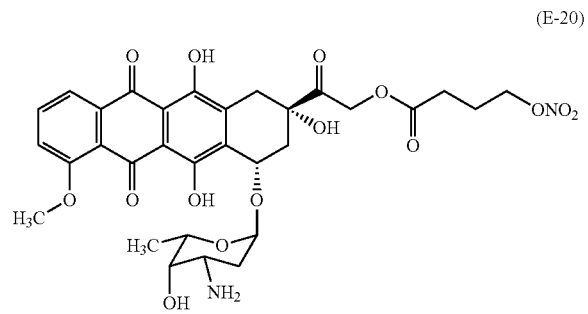

(E-20)

The precursor drug is doxorubicin of formula:

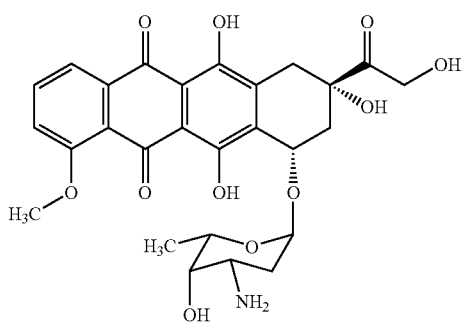

(E-20a)

The compound precursor of B is 4-hydroxy-butyric acid
Compound (E-20) is synthetized according to the process of Example 1. Yield: 12%
Elemental analysis:

| Calculated % | C 55.19 | H 5.08 | N 28.01 |
|---|---|---|---|
| Found % | C 55.21 | H 5.09 | N 28.08 |

EXAMPLE 21

Synthesis of (Z)-5-fluoro-2-methyl-1-[[4-(methyl sulphinyl) phenyl]methylene]-1H-indene-3-acetic acid (4-nitroxy)butyl ester of formula:

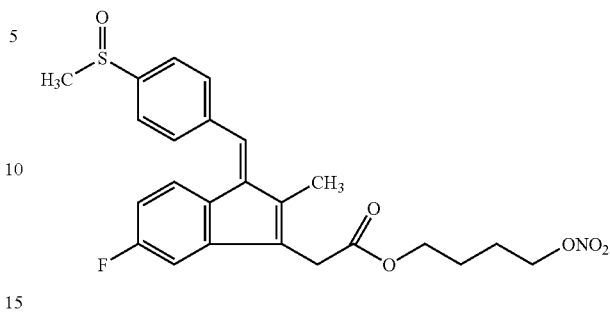

(E-21)

The precursor drug is Sulindac of formula:

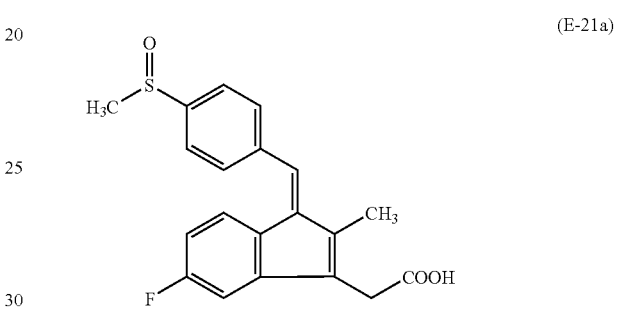

(E-21a)

and the precursor of B is 1,4-butandiolo a) Preparation of cis-5-fluoro-2-methyl-1-[p-(methy sulphinyl)benzyliden]indene-3-acetic acid 4-bromo butil ester To a solution of sulindac (5.17 g, 14.5 mmole) in dimethylformamide (50 ml) EtONa (1.18 g, 16.4 mmole) is added. The reaction mixture is kept under stirring for one hour, then a solution of 1,4-dibromobutane in dimethylformammide (20 ml) is added.

The reaction mixture is stirred at room temperature for 8 hours, then diluted with ethyl ether and washed with water. The organic phase is dehydrated on sodium sulphate and then evaporated at a reduced pressure. The raw product thus obtained is purified by column chromatography on silica gel, the eluent being n-hexane/ethyl acetate 3/7 (ratio by volume). It is obtained cis-5-fluoro-2-methyl-1-[p-(methylsulfinyl) benzyliden]indene-3-acetic acid 4-bromobutyl ester.

b) Preparation of cis-5-fluoro-2-methyl-1-[p-(methyl sulphinyl)benzyliden]indene-3-acetic acid 4-(nitroxy)butyl ester To a solution of cis-5-fluoro-2-methyl-1-[p-(methylsulfinyl) benzyliden]indene-3-acetic acid 4-bromobutyl ester (5.01 g, 10.18 mmole) in acetonitrile (60 ml) silver nitrate is added (3.5 g, 20.6 mmole). The reaction mixture is stirred at a temperature of 80° C. for 48 hours in the absence of light, then cooled at room temperature and filtered to remove the formed insoluble silver salts and evaporated under a reduced pressure. The residue is purified by column chromatography on silica gel, eluted with n-hexane/ethyl acetate 3/7 (ratio by volume). After evaporation of the solvent it is obtained (Z)-5-fluoro-2-methyl-1-[[4-(methyl sulphinyl)phenyl]methylene]-1H-indene-3-acetic acid (4-nitroxy)butyl ester (m.p. 93-97). Yield 40%.

Elemental analysis:

| Calc. % | C 60.87 | H 5.11 | F 4.01 | N 2.96 | S 6.77 |
|---|---|---|---|---|---|
| Found % | C 60.85 | H 5.13 | F 3.93 | N 2.94 | S 6.75 |

Example F8

Example F1 was repeated with three groups of rats (each group of ten animals), all of them receiving NEM, and orally administered as it follows :
a. control group: the vehicle formed of an aqueous suspension 1% w/v of carboxymethylcellulose,
b. one group (group b-comparative) administered at the same time with 10 mg/Kg (0.034 mmoles/Kg) of diclofenac+4 mg/Kg (0.034 mmoles/Kg) of N-methyldiethanolamine in the same above vehicle,
c. one group (group c) administered with 15 mg/Kg (0.034 mmoles/Kg) of the ester derivative of diclofenac according to the invention (ref. ex. 14), in the above same vehicle.

The results are reported in Table VIII and show that the mixture administered to group b (comparative), was much less effective in reducing gastric lesions than the group (group c) treated with the derivative according to the invention.

Example F9

Antiinflammatory and analgesic activity of 4-(nitrooxy) butanoic acid 4-(N-acetylamino)phenyl ester (NO-paracetamol) and of the precursor paracetamol.

Foreword

The principal therapeutic effects of NSAIDs derives from their ability to inhibit prostaglandin production ("Goodman & Gilman's, The Pharmacological Basis of Therapeutics", 9th Ed. 1996, McGraw Hill page 620) and the agents are classified on the basis of said principle. Sulindac and paracetamol have different mechanism from most currently used NSAIDS in view of their negligible ability to inhibit prostaglandin production. Both they interact with oxygen free radicals.

Antiinflammatory and analgesic activity have been measured according to carrageenan rat paw edema and acetic acid mouse writhing methods. Rats (male, wistar 100-150 g. and mice (male, LACA, 22-35 g) were used. NO-paracetamol, paracetamol or vehicle were given as carboxymethylcellulose suspension (0.5% w/v) in a volume of 1 mg/Kg.

Carrageenan Paw Edema

Experiments were conducted as described by Al-Swayeh et al., Brit. J. Pharmacol. 129, 343-350 2000). Hind paw volume was determined by plethysmography before and after 3 h after interplantar carrageenan injection (100 microliter, 2% w/v). The compounds were given intraperitoneally 15 ml prior to carrageenan injection. At the end of the experiment animals were killed by cervical dislocation and exsanguination. The Results shown in Table IX are expressed as % of paw edema inhibition, i.e. the paw volume of the controls (vehicle) subtracted of the paw volume of the treated and the obtained difference divided by the paw volume of the controls.

Acetic Acid Writhing

Experiments were conducted as described by Moore et al. (Br. J. Pharmacol. 102, 198-202 1990). The compounds were given orally 15 minutes prior to intraperitoneal acetic acid (2% w/v in saline pH 2.7, 10 ml/Kg). Mice were transferred immediately to individual observation cages and the number of abdominal constrictions monitored over the following 30 minutes. At the end of the observation period the animals were killed by cervical dislocation and exsanguination. Results are expressed as the number of abdominal costrictions (writhings) per 30 minutes test period, expressed as percentage to those observed in the control group, and are reported in Table IX.

The results of the Table demonstrate that NO-paracetamol is much more active in both tests than paracetamol.

Example F10

Liver safety following administration of NO-paracetamol and paracetamol

Rats received either NO-paracetamol (1.4 g/Kg i.p.) or paracetamol (1.16 g/Kg i.p.) or vehicle (0.9% w/v NaCl containing 20% v/v tween-20). After 6 hours the animals were killed by cervical dislocation, trunk blood collected and plasma analysed for aspartate aminotransferase (AST) and alanine aminotransferase (ALT) activity, liver glutathione and bilirubin concentration.

Glutathione depletion induced by paracetamol is considered a sign of oxidative stress (B. Halliwell, J. Gutterbridge "Free radicals in biology and medicine" 1993, Clarendon Press, pages 334-335).

The results are reported in Table X and are expressed as the percentage calculated on the corresponding values of the vehicle group (100%).

The results demonstrate that administration of paracetamol causes hepatic damage, as from the values of transaminases AST and ALT, and of bilirubin in respect of those of the controls.

Administration of NO-paracetamol induces much lower increases of AST and ALT, whereas the bilirubin concentration is lower than that in the control groups.

Thus, unlike pracetamol, NO-paracetamol is able to spare the liver, even in conditions of oxidative stress (i.e. hepatic glutathione is similarly depleted with paracetamol and NO-paracetamol).

TABLE I

Test 1: Gastric tolerability of drugs representative of the drug classes illustrated in the present invention in animals not treated or treated with NEM (oxidative stress conditions). The % incidence is calculated from the ratio between the number of animals found with gastric lesions and that total of the group.

| Compound | dose (mg/Kg)/ admin. route | Gastro-enteropathy (% incidence) | |
|---|---|---|---|
| | | without NEM | with NEM |
| carrier | | 0 | 0 |
| Indomethacin | 7.5/p.o. | 0 | 100 |
| Ambroxol | 25/p.o. | 0 | 80 |
| Mesalamine | 750/i.c. | 0 | 60 |
| Alendronate | 15/p.o. | 0 | 90 |
| Tacrine | 1/s.c. | 0 | 100 |
| Omeprazol | 30/s.c. | 0 | 0 |
| Misoprostol | 0.5/s.c. | 0 | 0 | p.o. = per os;
i.c. = by intracolonic route;
s.c. = by subcutaneous route.

TABLE II

Test 2: Inhibition of apoptosis (DNA fragmentation) induced by CIP in the endothelial cells in the presence of compounds representative of the drug classes illustrated in the present invention.

| Compound | Apoptosis % with respect to the controls treated only with CIP |
|---|---|
| Indomethacin | 95 |
| Paracetamol | 120 |
| Clopidogrel | 110 |
| Salbutamol | 90 |
| Ambroxol | 70 |
| Alendronate | 160 |
| Diphylline | 95 |
| Cetirizine | 115 |
| Enalapril | 80 |
| Nicotinamide | 98 |
| Doxorubicin | 94 |
| Acyclovir | 95 |
| Mesalamine | 74 |
| Tacrine | 90 |
| Simvastatin | 72 |
| Omeprazol | 90 |

TABLE III

Test 5: Screening of the effectiveness of the listed substances to inhibit radical production induced by $Fe^{II}$

| Compound | % Radical inhibition from $Fe^{II}$ |
|---|---|
| blank | 0 |
| N-methyldiethanolamine | 0 |
| Diethylenglycol | 0 |
| 1,4-Butandiol | 0 |
| Thiodiethyleneglycol | 0 |

TABLE IV

Test 3: Gastric tolerability (gastrointestinal damage incidence), hepatic (GPT dosage, glutamic-pyruvic transaminase), and cardiovascular (blood pressure) of some compounds representative of the drug classes illustrated in the present invention under conditions of endothelial trouble induced by L-NAME. The results relating to the blood pressure and GPT are expressed as % values compared with those found in animals treated with the only carrier, without L-NAME.

| Compound | dose mg/kg/ administ. route | Blood pressure % without L-NAME | Blood pressure % with L-NAME | GPT % without L-NAME | GPT % with L-NAME | Gastroenteropathy % without L-NAME | Gastroenteropathy % with L-NAME |
|---|---|---|---|---|---|---|---|
| Carrier | | 100 | 152 | 100 | 155 | 0 | 30 |
| Paracetamol | 300/i.p. | 108 | 155 | 180 | 500 | 20 | 90 |
| Doxorubicin | 1/i.p. | 120 | 145 | 195 | 360 | 30 | 100 |
| Simvastatin | 50/p.o. | 85 | 148 | 122 | 220 | 0 | 60 |
| Omeprazol | 30/s.c. | 100 | 150 | 100 | 160 | 0 | 10 |
| Misoprostol | 0.5/s.c. | 100 | 142 | 100 | 160 | 0 | 5 |

TABLE V

Test 4A: Screening of the effectiveness of the listed substances to inhibit erythrocyte haemolysis induced by cumene hydroperoxide

| Compound | % Haemolysis inhibition |
|---|---|
| N-Methyldiethanolamine | 54.4 |
| Diethylenglycol | 33.4 |
| Thiodiethylenglycol | 26 |
| 1,4-Butandiol | 17.4 |
| Butanol | 10.5 |
| Diethanolamine | 2.5 |

TABLE VI

Experiment F6: Apoptosis inhibition (DNA fragmentation) induced in endothelial cells by hydrogen peroxide, by precursors representative of the drug classes described in the present invention and of the corresponding derivatives of the invention.

| Compound | Apoptosis % (respect to the controls treated only with CIP) |
|---|---|
| Carrier | 0 |
| Diclofenac (comp.) | 15 |
| Diclofenac nitroxyester Es. 14 | 72 |
| Ambroxol (comp.) | 25 |
| Ambroxol nitroxyester Ex. 3 | 50 |
| Alendronate (comp.) | 18 |
| Alendronate nitroxyester Ex. 4 | 54 |
| Tacrine (comp.) | 8 |

TABLE VI-continued

Experiment F6: Apoptosis inhibition (DNA fragmentation) induced in endothelial cells by hydrogen peroxide, by precursors representative of the drug classes described in the present invention and of the corresponding derivatives of the invention.

| Compound | Apoptosis % (respect to the controls treated only with CIP) |
|---|---|
| Tacrine nitroxyester Ex. 11 | 73 |

TABLE VII

Experiment F7: screening of the gastric tolerability of the derivatives according to the present invention compared with that of the precursor drugs

| Treatment | dose mg/kg | Gastropathy % incidence |
|---|---|---|
| Carrier | — | 0 |
| Diclofenac (comp.) | 20 p.o. | 70 |
| Diclofenac nitroxyester Es. 14 | 20 p.o. | 0 |
| Ambroxol (comp.) | 100 p.o. | 60 |
| Ambroxol nitroxyester Ex. 3 | 100 p.o. | 10 |
| Alendronate (comp.) | 100 p.o. | 100 |
| Alendronate nitroxyester Ex. 4 | 100 p.o. | 10 |
| Tacrine (comp.) | 10 p.o. | 60 |
| Tacrine nitroxyester Ex. 11 | 10 s.c. | 20 |

TABLE VIII

Test on gastric tolerability following oral administration of NEM (Ex. F8)

| groups | dose mg/Kg p.o. | Gastropathy % incidence |
|---|---|---|
| controls | — | — |
| group b - comparative mixture diclofenac (A) + N-methyldiethanolamine (B) | 10(A) + 4(B) | 50 |
| group c diclofenac derivative according to the invention (ref. ex. 14) | 14 | 20 |

TABLE IX

Antiinflammatory and analgesic activity of NO-paracetamol and paracetamol.

| Treatment | Antiinflammatory activity % paw edema inhibition | Analgesic activity % writhing inhibition |
|---|---|---|
| vehicle | — | — |
| paracetamol | 34 | 40 |
| NO-paracetamol | 69 | 490 |

TABLE X

Liver safety assayed by AST (aspartate aminotransferase) ALT (alanine aminotransferase), glutathione and bilirubin concentration in animals treated with NO-paracetamol and paracetamol. The values given in the Table are expressed as % to the corresponding of the control group.

| Treatment | AST % | ALT % | Glutathione % | Bilirubin % |
|---|---|---|---|---|
| vehicle | 100 | 100 | 100 | 100 |
| paracetamol | 330 | 171 | 52 | 200 |
| NO-paracetamol | 160 | 57 | 49 | 136 |

The invention claimed is:

1. Compounds or their salts having the following general formula (I):

A-B-N(O)$_s$     (I)

wherein:
s is an integer equal to 1 or 2;
A=R-T$_1$-, wherein
  R is a drug radical wherein the drug is naproxen; and
  T$_1$=(CO)$_t$ or (X)$_{t'}$, wherein X=O, S, NR$_{1c}$, R$_{1c}$ is H or a linear or branched alkyl, having from 1 to 6 carbon atoms, or a free valence, t and t' are integers and equal to zero or 1, with the proviso that t=1 when t'=0; t=0 when t'=1;
B=-T$_B$-X$_2$—O— wherein
  T$_B$=(CO) when t=0, T$_B$=X when t'=0, X being as above defined;
  X$_2$ is equal to R$_{1B}$-X-R$_{2B}$ radical wherein X is S or NR$_{1c}$ wherein NR$_{1c}$ is as above defined, R$_{1B}$ and R$_{2B}$, equal to or different from each other, are linear or branched C$_1$-C$_6$ alkylenes, or X$_2$ is a radical wherein two alkylene chains C$_1$-C$_4$ are linked to nonadjacent positions of a central ring having 4 or 6 atoms, said ring being an unsaturated cycloaliphatic ring, or a saturated or aromatic heterocyclic ring, containing one or two heteroatoms, equal or different, selected from O, S, N; wherein the unsaturated cycloaliphatic ring does not have aromatic character according to Huckel's rule.

2. Compounds according to claim 1, wherein precursor compounds of B having formula T$_B$-X$_2$—OH are: N-methyldiethanolamine: HO—(CH$_2$)2—N(CH$_3$)—(CH$_2$)$_2$—OH, thiodiethylenglycol: HO—(CH$_2$)$_2$—S—(CH$_2$)$_2$—OH, 1,4 dioxane-2,6-dimethanol, tetrahydropyrane-2,6-dimethanol, 4H pyrane-2,6-dimethanol, tetrahydrothiopyrane-2,6-dimethanol, 1,4-dithiane-2,6-dimethanol, cyclohexene-1,5-dimethanol, thiazole-2,5-dimethanol, thiophene-2,5-dimethanol, or oxazole-2,5-dimethanol.

3. Pharmaceutical formulations containing as active principle the compounds or their salts according to claim 1.

4. Compounds according to claim 1, wherein s=2.

5. Compounds according to claim 1, wherein X$_2$ is a radical wherein two alkylene chains C$_1$-C$_2$ are linked to nonadjacent positions of the central ring.

6. Compounds according to claim 1, wherein the central ring has 5 or 6 atoms.

7. Compounds according to claim 1, wherein precursor compounds of B having formula T$_B$-X$_2$—OH are N-methyldiethanolamine, diethylenglycol, or thiodiethylenglycol.

* * * * *